(12) United States Patent
Broeng et al.

(10) Patent No.: US 11,433,253 B2
(45) Date of Patent: Sep. 6, 2022

(54) LIGHT THERAPY SYSTEM AND METHODS OF USE

(71) Applicants: The Regents of the University of California, Oakland, CA (US); Danmarks Tekniske Universitet, Kgs. Lyngby (DK)

(72) Inventors: Jes Broeng, Birkeroed (DK); Paul Michael Petersen, Hilleroed (DK); Ngoc Mai Thi Nguyen, San Jose, CA (US); Lance Kriegsfeld, Berkeley, CA (US)

(73) Assignees: The Regents of the University of California, Oakland, CA (US); Danmarks Tekniske Universitet, Kgs. Lyngby (DK)

( * ) Notice: Subject to any disclaimer, the term of this patent is extended or adjusted under 35 U.S.C. 154(b) by 0 days.

(21) Appl. No.: 16/775,131

(22) Filed: Jan. 28, 2020

(65) Prior Publication Data
US 2020/0164220 A1 May 28, 2020

Related U.S. Application Data

(63) Continuation of application No. 16/486,136, filed as application No. PCT/US2018/018250 on Feb. 14, 2018.
(Continued)

(51) Int. Cl.
*A61N 5/06* (2006.01)
(52) U.S. Cl.
CPC ......... *A61N 5/0618* (2013.01); *A61N 5/0622* (2013.01); *A61N 2005/0651* (2013.01); *A61N 2005/0663* (2013.01)

(58) Field of Classification Search
CPC .. A61N 5/0618; A61N 5/0622; A61N 5/0651; A61N 5/0663
See application file for complete search history.

(56) References Cited

U.S. PATENT DOCUMENTS 9,352,170 B1 * 5/2016 Davis .................. A61N 5/0618
10,129,937 B1 * 11/2018 Lin ........................ H05B 45/14
(Continued)

FOREIGN PATENT DOCUMENTS

| CN | 108697889 A | 10/2018 |
| JP | 2012524369 A | 10/2012 |

(Continued)

OTHER PUBLICATIONS

L. Aron and B. Yankner, "Neural synchronization in Alzheimer's disease", Nature, vol. 540, No. 7632, pp. 207-208, 2016. Available: 10.1038/540207a. (Year: 2016).*
(Continued)

*Primary Examiner* — Lynsey C Eiseman
*Assistant Examiner* — Amanda L. Steinberg
(74) *Attorney, Agent, or Firm* — Tom Hunter; Weaver Austin Villeneuve & Sampson LLP

(57) ABSTRACT

In certain embodiments a light therapy system (e.g., phototherapy device), such as for treatment of Alzheimer's disease, depression, dementia, short-term memory, or for improved learning, improved athletic performance or improved cognitive performance, is provided where the light system comprises a blue light source that operates at a frequency in the range from 20 to 50 Hz (preferably around 40 Hz), whereby the system enables retinal ganglion cells of a human to be exposed in order to stimulate brain waves (gamma oscillations in the human's brain).

29 Claims, 15 Drawing Sheets

Related U.S. Application Data

(60) Provisional application No. 62/595,065, filed on Dec. 5, 2017, provisional application No. 62/459,138, filed on Feb. 15, 2017.

(56) References Cited

U.S. PATENT DOCUMENTS

| | | | |
|---|---|---|---|
| 2006/0239689 A1* | 10/2006 | Ashdown | H05B 45/20 398/130 |
| 2008/0125836 A1 | 5/2008 | Streeter et al. | |
| 2009/0005837 A1 | 1/2009 | Olmstead | |
| 2009/0023977 A1 | 1/2009 | Sperling et al. | |
| 2010/0016841 A1 | 1/2010 | De Taboada et al. | |
| 2010/0174345 A1 | 7/2010 | Ashdown | |
| 2011/0084614 A1* | 4/2011 | Eisele | H05B 33/0851 315/152 |
| 2012/0095534 A1 | 4/2012 | Schlangen et al. | |
| 2014/0058483 A1 | 2/2014 | Zao et al. | |
| 2014/0128941 A1* | 5/2014 | Williams | H05B 45/46 607/88 |
| 2016/0008568 A1 | 1/2016 | Attia et al. | |
| 2016/0158487 A1* | 6/2016 | Colbaugh | A61N 5/0618 607/88 |
| 2017/0105265 A1* | 4/2017 | Sadwick | F21K 9/238 |
| 2017/0143934 A1 | 5/2017 | Tsai et al. | |
| 2017/0304584 A1 | 10/2017 | Tsai et al. | |
| 2019/0105509 A1 | 4/2019 | Tsai et al. | |
| 2019/0126062 A1 | 5/2019 | Adaikkan et al. | |
| 2019/0209806 A1* | 7/2019 | Allen | G05B 15/02 |
| 2019/0240443 A1 | 8/2019 | Tsai et al. | |
| 2020/0269065 A1 | 8/2020 | Broeng et al. | |

FOREIGN PATENT DOCUMENTS

| | | | |
|---|---|---|---|
| JP | 2015512951 A | 4/2015 | |
| JP | 2016525408 A | 8/2016 | |
| WO | WO-2010122446 A1 | 10/2010 | |
| WO | WO-2013155505 A1 | 10/2013 | |
| WO | WO-2014143896 A2 | 9/2014 | |
| WO | WO 2015/011652 A1 | 1/2015 | |
| WO | WO-2016145059 A1 | 9/2016 | |
| WO | WO 2018/152255 A1 | 8/2018 | |

OTHER PUBLICATIONS

PCT International Search Report and Written Opinion dated Jun. 6, 2018 issued in PCT/US2018/018250.

PCT International Preliminary Report on Patentability and Written Opinion dated Aug. 20, 2019 issued in PCT/US2018/018250.

Iaccarino et al. (2016) "Gamma frequency entrainment attenuates amyloid load and modifies microglia." *Nature* 540: 230-235, [HHS Public Access—Author Manuscript—37 pages] https://doi.org/10.1038/nature20587.

Vandewalle et al. (2010) "Spectral quality of light modulates emotional brain responses in humans." *PNAS* 107(45): 19549-19554.

Iaccarino et al. (2016) "Gamma frequency entrainment attenuates amyloid load and modifies microglia." *Nature* 540(7632): 230-252 (23 pages).

U.S. Appl. No. 16/486,136, filed Aug. 14, 2019, Broeng et al.

De Lange et al Eye's response at flicker fusion to square-wave modulation of a test field surrounded by a large steady field of equal mean luminance. J. opt. Soc. Amer. 51, 415-421 (1961).

EP Extended Search Report dated Oct. 28, 2020 issued in EP 18754662.7.

EP Supplemental Partial Search Report dated Jul. 10, 2020 issued in EP 18754662.7.

JP Office action dated Oct. 25, 2021, in JP Application No. JP20190543972 with English translation.

Magnussen et al. (1974) "Brightness and Darkness Enhancement During Flicker: Perceptual Correlates of Neuronal B- and D-Systems in Human Vision." Exp. Brain Res. 22: 399-413.

U.S. Final Office Action dated Oct. 7, 2021 issued in U.S. Appl. No. 16/486,136.

U.S. Office Action dated Dec. 17, 2020 issued in U.S. Appl. No. 16/486,136.

* cited by examiner

LIGHT THERAPY SYSTEM AND METHODS OF USE

CROSS-REFERENCE TO RELATED APPLICATIONS

This application is a continuation of U.S. Ser. No. 16/486,136, filed on Aug. 14, 2019, which is a U.S. 371 National Phase of PCT/US2018/018250, filed on Feb. 14, 2018, which claims benefit of and priority to U.S. Ser. No. 62/595,065, filed on Dec. 5, 2017, and to U.S. Ser. No. 62/459,138, filed on Feb. 15, 2017, all of which are incorporated herein by reference in their entirety for all purposes.

STATEMENT OF GOVERNMENTAL SUPPORT

Not Applicable

BACKGROUND

Several studies have shown that light intensity and the color/hue of light impacts human health, and various health-related technologies based on illumination have been proposed (see, e.g., PCT Publication: WO 91/14475, U.S. Pat. No. 5,447,528, and references therein). In recent years, blue light sources, systems comprising such sources, and wearables monitoring and recommending on blue light exposure have gain interest (see for example US Patent Pub: 2013/011891, WO 2015/200730, WO 2012/146256, US 2016/027282).

The reason is that blue light affects circadian rhythms, as the eyes contain photoreceptors with high sensitivity for blue light, and these photoreceptors regulate melatonin, also known as the "sleep hormone" (see e.g. Brainard et al. (2001) *J. Neurosci.* 21: 6405-6412). Additionally, these photoreceptors and their exposure to blue light are believed to regulate serotonin, also known as the "happiness" hormone (see e.g. Vandewalle et al. (2010) *Proc. Natl. Acad. Sci. USA*, 107: 19549-19554. It is further speculated that other health and psychological effects may be influenced via blue light, such as depression, dementia, short-term memory and learning.

Recent results in neuroscience (Iaccarino et al. (2016) *Nature* 540(8): 230-252) have indicated that Alzheimer's disease, a neural disorder, may be treated by exposure to flashing lights that stimulate the brain's immune cells to remove toxic proteins causing the disease. These results were obtained in laboratory studies of rodents (mice) with highly controlled environments, where rodents are exposed to stroboscopic light exposure lasting at least 1 hour. The stroboscopic light typically operated at a frequency of 40 Hz and helped stimulate and restore synchronized brain activity, known as gamma oscillations, which is linked to attention and memory.

While the results are encouraging for mice there are no studies of humans. And there are barriers to translate the methods to humans. One of the problems is related to difficulties in controlling the environment for humans in real life. It is possible that pulsing or blinking of light can synchronize neuron activity and this might be beneficial to old people with dementia or subjects with Alzheimer's disease since the neuron activity will improve and lead to better memory and coordination of human activities. However, even though blinking/flashing light sources may be therapeutically effective it is believed they will produce significant side effects in humans (or non-human mammalian subjects) such as visual glare, visual fatigue, ocular discomfort, headache, possible convulsions in epileptics, and the like. Also, it is known that blinking light around 60 Hz is stressful to humans and animals.

Therefore, it is problematic to expose humans to stroboscopic light in a manner as was done for the rodent studies. Further disadvantages of such stroboscopic light include provocation of elliptic conditions, distraction of attention, feelings of being uncomfortable, etc.

Furthermore, it is a disadvantage for use in humans that exposure to flickering light over extended time (an hour or longer) is required. This may be impractical for a broad range of people.

SUMMARY

The wavelength sensitivity of the receptors in the retina for our vision that form images is different from the wavelength sensitivity of the receptors that control our hormone system and brain activities that are associated with emotions, memory, and leaning. Using these recent discoveries, it was possible to develop a therapeutic lamp (phototherapy device) that modulates the neuron responses in different parts of the brain (such as the hippocampus) without affecting or almost without affecting the vision. In certain embodiments, the lamp will typically modulate the brain activity with 30-60 Hz. However, when humans look into the lamp they will not see the stroboscopic effects. This is in contrast to ordinary lamps with 30-60 Hz flicker. The purpose of the phototherapy device is to modulate the brain response for humans with Alzheimer's disease and at the same time reduce side effects due to visual discomfort of the blinking light.

Accordingly, in certain embodiments, a light therapy system (e.g., a phototherapy device) is disclosed herein for treatment of Alzheimer's disease, depression, dementia, short-term memory, or for improved learning, improved athletic performance or improved cognitive performance. In certain embodiments the light system comprises a blue light source that operates at a frequency in the range from 20 to 50 Hz (preferably around 40 Hz), whereby the system enables retinal ganglion cells of a human to be exposed in order to stimulate brain waves (gamma oscillations in the human's brain).

In certain embodiments aspects a light therapy system is disclosed herein that operates over an extended time during a person's sleep. Typically, the extended time is one hour or more (for example continuously over an hour or in multiple time segments that total more than an hour per night). In certain embodiments the system comprises a sleep mask that comprises a stroboscopic blue light source that operates at a frequency in the range from 20 to 50 Hz (preferably around 40 Hz). The present inventors have further realized a method where a person uses such a system, wherein the stroboscopic blue light source illuminates a person's eyelids during sleep. The system enables retinal ganglion cells to be exposed be a fraction of the emitted stroboscopic blue light in a sufficient time and intensity to positively affect or stimulate desired parts of the brain.

In certain embodiments a new light therapy system is provided that comprises a lamp or a luminaire, such as a lamp or luminaire positioned in a room, from a ceiling or a stationary lamp. In certain embodiments the system comprises a narrow spectrum light source with a peak intensity in the blue part of the light spectrum (preferably around 460 nm) and a broad-spectrum light source covering a majority or all of the visible light spectrum, wherein the narrow spectrum light source is a stroboscopic blue light source that operates at a frequency in the range from 20 to 50 Hz (preferably around 40 Hz). In certain embodiments the power of emitted radiation from the narrow spectrum light source is less than the power of emitted radiation from the broad-spectrum light source, such as in the range from 1% to 50%, such as in the range from 1% to 10%.

In certain embodiments a light therapy system is described herein that uses two light sources comprising different wavelengths. FIG. 2 shows chromaticity diagram from which it can be seen that a specific white light color can be generated with different wavelengths combinations. As an example of one preferred embodiment, a system is provided, where a first light source comprises the wavelengths 460 nm, 650 nm, and 570 nm, and a second light source comprises the wavelengths 490 nm, 770 nm (or 670 nm) and 600nm. The system uses alternating combination of the light sources, such as a 50% duty cycle at 40 HZ. I.e. the first light source comprising 460 nm light is stroboscopic at 40 HZ and the second light source (that does not comprise light at 460 nm) is stroboscopic (e.g., blinking) at 40 HZ. The two light sources are substantially synchronized such that when the first light source is turned on, the second light source is turned off, and vice versa. Hence, the experience by a human is constant white light illumination, but the white light is composed of two different light sources of which one provides substantially more light from 440 nm to 480 nm at the non-visual ganglion cells at the retina and therefore increased brain activity via stroboscopic light around 460 nm. Alternative duty cycles are also within the scope of the invention, such as 10% duty cycle of the first light source and 90% duty cycle of the second light source (10/90), such as 5/95, such as 25/75, such as 75/25, such as 95/5.

In certain embodiments a light therapy system and method of its use is provided that enables positive stimulation of the brain without the aforementioned disadvantages. In particular, a light therapy system that may help patients with Alzheimer's disease is provided. The light therapy system that may also provide positive stimulation of the brain to healthy people, such as athletes, in order to optimize their performance.

Various embodiments contemplated herein may include, but need not be limited to, one or more of the following:

Embodiment 1: A phototherapy device, said device comprising:
- a first light source that produces a light that comprises or consists of a blue spectral component and/or green spectral component wherein light comprising said blue and/or green spectral component is a blinking light; and
- a second light source that produces a light lacking a blue and/or green spectral component or where the blue and/or green spectral component produced by said second light source is smaller than the blue and/or green spectral component of the light produced by said first light source, and where said second light source produces illumination that supplements the illumination produced by the first light source so that the blinking of said first light source when combined with the light from said second light source is substantially undetectable by human vision.

Embodiment 2: The phototherapy device of embodiment 1, wherein:
- said first light source produces a light that comprises or consists of a blue spectral component; and
- said second light source that produces a light lacking a blue spectral component or where the blue spectral component produced by said second light source is smaller than the blue spectral component of the light produced by said first light source.

Embodiment 3: The device according to any one of embodiments 1-2, wherein the blinking frequency and intensity of said first light source is sufficient to stimulate or to entrain brain waves in a human's brain when the human is exposed to said light source.

Embodiment 4: The device of embodiment 3, wherein said brain waves comprise gamma oscillations.

Embodiment 5: The device according to any one of embodiments 1-4, wherein the frequency of blinking of said first light source ranges from about 20 Hz, or from about 30 Hz, or from about 35 Hz or from about 40 Hz up to about 100 Hz, or up to about 80 Hz, or up to about 60 Hz, or up to about 50 Hz, or up to about 45 Hz.

Embodiment 6: The device of embodiment 5, wherein the frequency of blinking of said first light source ranges from about 20 Hz up to about 50 Hz.

Embodiment 7: The device of embodiment 5, wherein the frequency of blinking of said first light source is about 40 Hz.

Embodiment 8: The device according to any one of embodiments 1-7, wherein the duration of the blinks of said first light source ranges from about 1 ms, or from about 5 ms up to about 50 ms, or up to about 40 ms, or up to about 30 ms, or up to about 20 ms, or up to about 15 ms, or up to about 10 ms.

Embodiment 9: The device according to any one of embodiments 1-8, wherein the duration of the blinks of said first light source ranges from about 5 ms up to about 20 ms, or from about 8 ms up to about 15 ms.

Embodiment 10: The device according to any one of embodiments 1-9, wherein the color temperature of said first light source ranges from about 2700K, or from about 2800K, or from about 2900K up to about 6500K, or up to about 5000K, or up to about 4000K, or up to about 3500K.

Embodiment 11: The device of embodiment 10, wherein the color temperature of said first light sources ranges from about 2900K up to about 3100 K.

Embodiment 12: The device of embodiment 11, wherein the color temperature of said first light source is about 3000K.

Embodiment 13: The device according to any one of embodiments 1-12, wherein said first light source provides a luminous intensity ranging from about 10 lm, or from about 25 lm, or from about 50 lm, or from about 100 lm, or from about 500 lm, up to about 10,000 lm, or up to about 5,000 lm, or up to about 1000 lm.

Embodiment 14: The device according to any one of embodiments 1-13, wherein said first light source provides irradiance that is larger than 5 mW/nm/m$^2$ in a wavelength range from about 440 nm up to about 500 nm, or from about 450 nm up to about 490 nm, or from about 450 nm up to about 480 nm, or from about 450 nm up to about 470 nm, or from about 455 nm up to about 465 nm.

Embodiment 15: The device according to any one of embodiments 1-13, wherein said first light source provides light having a total illuminance and/or an illuminance of said blue spectral component of at least about 10 lux, or at least about 20 lux, or at least about 30 lux, or at least about 40 lux, or at least about 50 lux, or at least about 60 lux, or at least about 70 lux, or at least about 80 lux, or at least about 90 lux, or at least about 100 lux, or at least about 120 lux, or at least about 130 lux, or at least about 140 lux, or at least about 150 lux, or at least about 160 lux, or at least about 170 lux, or at least about 180 lux, or at least about 190 lux, or at least about 200 lux, or at least about 300 lux, or at least about 400 lux, or at least about 500 lux, or at least about 600 lux, or at least about 700 lux, or at least about 800 lux, or at least about 900 lux, or at least about 1000 lux.

Embodiment 16: The device according to any one of embodiments 1-13, where said second light source is a blinking light source.

Embodiment 17: The device of embodiment 16, wherein the frequency of blinking of said second light source ranges from about 20 Hz, or from about 30 Hz, or from about 35 Hz or from about 40 Hz up to about 100 Hz, or up to about 80 Hz, or up to about 60 Hz, or up to about 50 Hz, or up to about 45 Hz.

Embodiment 18: The device of embodiment 16, wherein the frequency of blinking of said second light source ranges from about 20 Hz up to about 50 Hz.

Embodiment 19: The device of embodiment 16, wherein the frequency of blinking of said second light source is about 40 Hz.

Embodiment 20: The device according to any one of embodiments 16-19, wherein the duration of the blinks of said second light source ranges from about 1 ms, or from about 5 ms up to about 50 ms, or up to about 40 ms, or up to about 30 ms, or up to about 20 ms, or up to about 15 ms, or up to about 10 ms.

Embodiment 21: The device according to any one of embodiments 16-19, wherein the duration of the blinks of said second light source ranges from about 5 ms up to about 20 ms, or from about 8 ms up to about 15 ms.

Embodiment 22: The device according to any one of embodiments 1-21, wherein the color temperature of said second light source ranges from about 2700K, or from about 2800K, or from about 2900K up to about 6500K, or up to about 5000K, or up to about 4000K, or up to about 3500K.

Embodiment 23: The device of embodiment 22, wherein the color temperature of said second light sources ranges from about 2900K up to about 3100 K.

Embodiment 24: The device of embodiment 23, wherein the color temperature of said second light source is about 3000K.

Embodiment 25: The device according to any one of embodiments 1-24, wherein said second light source provides a luminous intensity ranging from about 10 lm, or from about 25 lm, or from about 50 lm, or from about 100 lm, or from about 500 lm, up to about 10,000 lm, or up to about 5,000 lm, or up to about 1000 lm.

Embodiment 26: The device according to any one of embodiments 1-25, wherein the difference in color temperature between said first light source and said second light source is less than about 30K, or less than about 20K, or less than about 10K, or is less than about 5K.

Embodiment 27: The device of embodiment 26, wherein the difference in color temperature between said first light source and said second light source ranges from about 5K up to about 10K.

Embodiment 28: The device according to any one of embodiments 1-27, wherein the distance to the black body locus $D_{UV}$ for said first light source and said second light source is less than about 0.001, or less than about 0.0001.

Embodiment 29: The device of embodiment 28, wherein the distance to the blackbody locus $D_V$ for said first light source and said second light source is about 0.0001 or less.

Embodiment 30: The device according to any one of embodiments 1-29, wherein the difference in intensity between said first light source and said second light source is less than about 100 lux, or less than about 75 lux, or less than about 50 lux, or less than about 40 lux, or less than about 30 lux, or less than about 20 lux, or less than about 10 lux, or less than about 5 lux, or less than about 2 lux.

Embodiment 31: The device according to any one of embodiments 1-30, wherein the first light source and the second light source emit light in substantially the same direction.

Embodiment 32: The device of embodiment 31, wherein the difference in illumination angel between said first light source and said second light source is less than about 30 degrees, or less than about 25 degrees, or less than about 20 degrees, or less than about 15 degrees, or less than about 10 degrees, or less than about 5 degrees.

Embodiment 33: The device according to any one of embodiments 1-32, wherein said device is configured to operate said first light source out of phase with said second light source.

Embodiment 34: The device of embodiment 33, wherein the phase difference between said first light source and said second light source ranges from about 90 degrees to about 180 degrees.

Embodiment 35: The device of embodiment 34, wherein the phase difference between said first light source and said second light source is about 180 degrees so that when said first light source is on, said second light source is off and vice versa.

Embodiment 36: The device according to any one of embodiments 1-35, wherein the duty cycle of said first light source and/or said second light source ranges from about 5% up, or from about 10%, or from about 15%, or from about 20%, or from about 25%, or from about 30%, or from about 35%, or from about 40% up to about 90%, or up to about 85%, or up to about 80%, or up to about 75%, or up toa bout 70%, or up to about 65%, or up to about 60%.

Embodiment 37: The device of embodiment 36, wherein the duty cycle of said first light source and/or said second light source is about 50%.

Embodiment 38: The device according to any one of embodiments 1-37, wherein the ratio of duty cycle of said first light source to said second light source ranges from about 1:10 to about 10:1, or from about 1:5 to about 5:1, or from about 1:2 to about 2:1.

Embodiment 39: The device of embodiment 38, wherein the ratio of duty cycle of said first light source to said second light source is about 1:1.

Embodiment 40: The device according to any one of embodiments 1-39, wherein said first light source comprises or consists of a blue spectral component, a green spectral component, and an orange or red spectral component.

Embodiment 41: The device of embodiment 40, wherein said first light source comprises or consists of a lamp that emits primarily a blue light, a lamp that emits primarily a green light, and a lamp that emits primarily an orange and/or red light.

Embodiment 42: The device according to any one of embodiments 1-41, wherein the blue light comprising said first light source, or the blue spectral component of said first light source, or the blue light emitted by a lamp is in the wavelength range from about 440 nm up to about 495 nm, or from about 440 nm up to about 480 nm, or from about 450 nm up to about 480 nm, or from about 450 nm up to about 470 nm.

Embodiment 43: The device of embodiment 42, wherein the blue light comprising said first light source, or the blue spectral component of said first light source, or the blue light emitted by a lamp has a maximum emission at about 460 nm.

Embodiment 44: The device according to any one of embodiments 1-43, wherein the green light comprising said first light source, or the green spectral component of said first light source, or the green light emitted by a lamp comprising said second light source is primarily in the wavelength range from about 495 nm up to about 570 nm, or from about 500 nm, or from about 510 nm, or from about 520 nm, or from about 530 nm, or from about 540 nm, or from about 550 nm up to about 570 nm.

Embodiment 45: The device of embodiment 44, wherein the green light comprising said first light source, or the green spectral component of said first light source, or the green light emitted by a lamp is primarily in the wavelength range from about 550 nm up to about 570 nm.

Embodiment 46: The device of embodiment 45, wherein the green light comprising said first light source, or the green spectral component of said first light source, or the green light emitted by a lamp has a maximum emission at about 550 nm or at about 570 nm.

Embodiment 47: The device according to any one of embodiments 1-46, wherein the orange/red light comprising said first light source, or the orange/red spectral component of said first light source, or the orange/red light emitted by a lamp comprising said second light source is primarily in the wavelength range from about 590 nm up to about 750 nm, or from about 600 nm up to about 700 nm, or up to about 650 nm.

Embodiment 48: The device of embodiment 47, wherein the orange/red light comprising said first light source, or the orange/red spectral component of said first light source, or the orange/red light emitted by a lamp is primarily in the wavelength range from about 600 nm up to about 650 nm.

Embodiment 49: The device of embodiment 48, wherein the orange/red light comprising said first light source, or the orange/red spectral component of said first light source, or the orange/red light emitted by a lamp has a maximum emission at about 600 nm or at about 650 nm.

Embodiment 50: The device according to any one of embodiments 1-49, wherein:
said second light source comprises or consists of a blue/green spectral component, an orange spectral component, and a red/far red spectral component; or
said second light source comprises or consists of a green spectral component, and an orange/red spectral component.

Embodiment 51: The device of embodiment 50, wherein:
said second light source comprises or consists of a lamp that emits primarily a blue/green light, a lamp that emits primarily an orange light, and a lamp that emits primarily a red/far red light; or
said second light source comprises or consists of a lamp that emits primarily a green light, and a lamp that emits primarily an orange/red light.

Embodiment 52: The device of embodiment 51, wherein said second light source comprises or consists of a lamp that emits primarily a blue/green light, a lamp that emits primarily an orange light, and a lamp that emits primarily a red/far red light.

Embodiment 53: The device of embodiment 52, wherein the blue/green light comprising said second light source, or the blue/green spectral component of said second light source, or the blue/green light emitted by a lamp comprising said second light source is primarily in the wavelength range from about 490 nm up to about 570 nm, or from about 500 nm, or from about 510 nm, or from about 520 nm, or from about 530 nm, or from about 540 nm, or from about 550 nm up to about 570 nm.

Embodiment 54: The device of embodiment 53, wherein the blue light comprising said second light source, or the blue spectral component of said second light source, or the blue light emitted by a lamp has a maximum emission at about 490 nm.

Embodiment 55: The device according to any one of embodiments 52-54, wherein the orange light comprising said second light source, or the orange spectral component of said second light source, or the orange light emitted by a lamp comprising said second light source is primarily in the wavelength range from about 590 nm up to about 620 nm, or from about 590 nm up to about 610 nm.

Embodiment 56: The device of embodiment 55, wherein the orange light comprising said second light source, or the orange spectral component of said second light source, or the orange light emitted by a lamp comprising said second light source has a maximum emission about 600 nm.

Embodiment 57: The device according to any one of embodiments 52-56, wherein the red/far red light comprising said second light source, or the red/far red spectral component of said second light source, or the red/far red light emitted by a lamp comprising said second light source is primarily in the wavelength range from about 620 nm, up to about 770 nm, or from about 650 nm up to about 750 nm, or from about 670 nm up to about 700 nm.

Embodiment 58: The device of embodiment 57, wherein the red/far red light comprising said second light source, or the red/far red spectral component of said second light source, or the red/far red light emitted by a lamp comprising said second light source is primarily is 670 nm or about 770 nm.

Embodiment 59: The device of embodiment 51, wherein said second light source comprises or consists of a lamp that emits primarily a green light, and a lamp that emits primarily an orange/red light.

Embodiment 60: The device of embodiment 59, wherein the green light comprising said second light source, or the green spectral component of said second light source, or the green light emitted by a lamp comprising said second light source is primarily in the wavelength range from about 495 nm up to about 570 nm, or from about 500 nm, or from about 510 nm, or from about 520 nm, or from about 530 nm, or from about 540 nm, or from about 550 nm up to about 570 nm.

Embodiment 61: The device of embodiment 60, wherein the green light comprising said second light source, or the green spectral component of said second light source, or the green light emitted by a lamp is primarily in the wavelength range from about 500 nm up to about 550 nm.

Embodiment 62: The device of embodiment 61, wherein the green light comprising said second light source, or the green spectral component of said second light source, or the green light emitted by a lamp has a maximum emission at about 500 nm.

Embodiment 63: The device according to any one of embodiments 59-62, wherein the orange/red light comprising said second light source, or the orange/red spectral component of said second light source, or the orange/red light emitted by a lamp comprising said second light source is primarily in the wavelength range from about 590 nm up to about 750 nm, or from about 600 nm up to about 700 nm, or up to about 650 nm.

Embodiment 64: The device of embodiment 63, wherein the orange/red light comprising said second light source, or the orange/red spectral component of said second light source, or the orange/red light emitted by a lamp is primarily in the wavelength range from about 600 nm up to about 650 nm.

Embodiment 65: The device of embodiment 64, wherein the orange/red light comprising said second light source, or the orange/red spectral component of said second light source, or the orange/red light emitted by a lamp has a maximum emission at about 600 nm or at about 610 nm.

Embodiment 66: The device according to any one of embodiments 1-65, wherein said phototherapy device produces a light that is perceived as a color other than white.

Embodiment 67: The device of embodiment 66, wherein said first light source comprises or consists of a green spectral component and a red spectral component and said second light source comprises a yellow spectral component.

Embodiment 68: The device according to any one of embodiments 66-67, wherein first light source comprises a green spectral component with a maximum emission at about 530 nm.

Embodiment 69: The device according to any one of embodiments 66-68, wherein said first light source comprises a red spectral component with a maximum emission at about a 630 nm.

Embodiment 70: The device according to any one of embodiments 66-69, wherein said second light source comprise or consists of a yellow spectral component.

Embodiment 71: The device of embodiment 70, wherein said second light source comprises a yellow spectral component with a maximum emission at about 580 nm.

Embodiment 72: The device of embodiment 66, wherein said first light source comprises or consists of a blue spectral component and a yellow spectral component.

Embodiment 73: The device of embodiment 72, wherein said first light source comprises a blue spectral component with a maximum emission at about 480nm.

Embodiment 74: The device according to any one of embodiments 72-73, wherein said first light source comprises a yellow spectral component with a maximum emission at about 575 nm.

Embodiment 75: The device according to any one of embodiments 72-74, wherein said second light source comprise or consists of a green spectral component and a red spectral component.

Embodiment 76: The device according to any one of embodiments 72-75, wherein said second light source comprises a green spectral component with a maximum emission at about 510 nm.

Embodiment 77: The device according to any one of embodiments 72-76, wherein said second light source comprises a red spectral component with a maximum emission at about 600 nm.

Embodiment 78: The device according to any one of embodiments 1-77, wherein said first light source comprises one or more light emitting diodes (LEDs).

Embodiment 79: The device of embodiment 78, wherein the first light source comprises at least one different LED for each spectral component.

Embodiment 80: The device according to any one of embodiments 1-79, wherein said second light source comprises one or more light emitting diodes.

Embodiment 81: The device of embodiment 80, wherein the second light source comprises at least one different LED for each spectral component.

Embodiment 82: The device according to any one of embodiments 1-81, wherein said first light source and said second light source are disposed in a diffuser.

Embodiment 83: The device according to any one of embodiments 1-82, wherein said device comprises a luminaire.

Embodiment 84: The device according to any one of embodiments 1-82, wherein said device comprises a table lamp or an overhead lamp.

Embodiment 85: The device according to any one of embodiments 1-82, wherein said device is configured for mounting proximate, at, and/or attached to a frame of a window.

Embodiment 86: The device according to any one of embodiments 1-82, wherein said device comprises a face or eye mask.

Embodiment 87: The device according to any one of embodiments 1-85, wherein said first light source and said second light source are in a single unit or housing.

Embodiment 88: The device according to any one of embodiments 1-85, wherein said first light source and said second light source are in different units or housings.

Embodiment 89: The device according to any one of embodiments 1-88, wherein said device comprises a controller that controls one or more of the intensity of said first light source and/or said second light source, the blinking rate of said first light source and/or said second light source, the phase of said first light source and/or said second light source, the spectral composition of said first light source and/or said second light source, and the intensity of said first light source and/or said second light source.

Embodiment 90: The device of embodiment 89, wherein said controller is configured to controls said first light source and/or said second light source as a function of the time of day.

Embodiment 91: The device according to any one of embodiments 89-90, said controller is configured to in response to movement in a room.

Embodiment 92: The device according to any one of embodiments 89-90, said controller is configured to interface with a computer, cell phone, or tablet.

Embodiment 93: A system comprising:
a device according to any one of embodiments 1-92; and
one or more of a personal health sensor configured to be worn by a human, a personal environment sensor, a cell phone configured with an application to interface with said device, a computer configured with an application not interface with said device, and a tablet configured to interface with said device.

Embodiment 94: The system of embodiment 93, wherein said system comprises one or more devices selected from the group consisting of a smart phone, a smart watch, an activity tracker, an ambient light sensor, a GPS, an accelerometer, and a clock.

Embodiment 95: A method of treating a subject having a neurodegenerative condition selected from the group consisting of dementia, mild cognitive impairment, and Alzheimer's disease, said method comprising:
exposing said subject to blinking blue light at a frequency ranging from about 20 Hz up to about 60 Hz, or from about 30 Hz up to about 50 Hz, or from about 35 Hz up to about 45 Hz, or at about 40 Hz, at an intensity and duration sufficient to mitigate a symptom, or slow or stop the progression of said neurodegenerative condition.

Embodiment 96: The method of embodiment 95, wherein said blue light comprises a blue light or a blue spectral component of a light in the wavelength range from about 440 nm up to about 495 nm, or from about 440 nm up to about 480 nm, or from about 450 nm up to about 480 nm, or from about 450 nm up to about 470 nm.

Embodiment 97: The method of embodiment 96, wherein the blue light or blue spectral component of a light has a maximum at about 460 nm.

Embodiment 98: The method according to any one of embodiments 96-97, wherein said blinking blue light is administered by a device according to any one of embodiments 1-92, or a system according to any one of embodiments 93-94.

Embodiment 99: The method according to any one of embodiments 95-98, wherein said method comprises ameliorating one or more symptoms of Alzheimer's disease, and/or reversing Alzheimer's disease, and/or reducing the rate of progression of Alzheimer's disease.

Embodiment 100: The method according to any one of embodiments 95-98, wherein said method comprises preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease.

Embodiment 101: The method of embodiment 100, wherein said method is a method of preventing or delaying the transition from a cognitively asymptomatic pre-Alzheimer's condition to a pre-Alzheimer's cognitive dysfunction.

Embodiment 102: The method of embodiment 100, wherein said method is a method of preventing or delaying the onset of a pre-Alzheimer's cognitive dysfunction, or ameliorating one or more symptoms of a pre-Alzheimer's cognitive dysfunction.

Embodiment 103: The method of embodiment 100, wherein said method comprises preventing or delaying the progression of a pre-Alzheimer's cognitive dysfunction (e.g., MCI) to Alzheimer's disease.

Embodiment 104: The method according to any one of embodiments 99-103, wherein said subject is a human.

Embodiment 105: The method according to any one of embodiments 99-104, wherein said subject exhibits biomarker positivity of AP in a clinically normal human subject age 50 or older.

Embodiment 106: The method according to any one of embodiments 99-104, wherein said subject exhibits asymptomatic cerebral amyloidosis.

Embodiment 107: The method according to any one of embodiments 99-106, wherein said subject exhibits cerebral amyloidosis in combination with downstream neurodegeneration.

Embodiment 108: The method according to any one of embodiments 99-107, wherein said subject exhibits cerebral amyloidosis in combination with downstream neurodegeneration and subtle cognitive/behavioral decline.

Embodiment 109: The method according to any one of embodiments 107-108, wherein said downstream neurodegeneration is determined by one or more elevated markers of neuronal injury selected from the group consisting of tau, and FDG uptake.

Embodiment 110: The method according to any one of embodiments 106-109, wherein said cerebral amyloidosis is determined by PET, or CSF analysis, and structural MRI (sMRI).

Embodiment 111: The method according to any one of embodiments 100-110, wherein said subject is a subject diagnosed with mild cognitive impairment.

Embodiment 112: The method according to any one of embodiments 100-111, wherein said subject shows a clinical dementia rating above zero and below about 1.5.

Embodiment 113: The method according to any one of embodiments 99-112, wherein the subject is at risk of developing Alzheimer's disease.

Embodiment 114: The method according to any one of embodiments 99-113, wherein the subject has a familial risk for having Alzheimer's disease.

Embodiment 115: The method according to any one of embodiments 99-113, wherein the subject has a familial Alzheimer's disease (FAD) mutation.

Embodiment 116: The method according to any one of embodiments 99-113, wherein the subject has the APOE ε4 allele.

Embodiment 117: The method according to any one of embodiments 100-116, wherein administration of said compound delays or prevents the progression of MCI to Alzheimer's disease.

Embodiment 118: The method according to any one of embodiments 95-117, wherein said method produces a reduction in the CSF of levels of one or more components selected from the group consisting of Aβ42, sAPPβ, total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio.

Embodiment 119: The method according to any one of embodiments 95-118, wherein said method produces a reduction of the plaque load in the brain of the subject.

Embodiment 120: The method according to any one of embodiments 95-119, wherein said method produces a reduction in the rate of plaque formation in the brain of the subject.

Embodiment 121: The method according to any one of embodiments 95-120, wherein said method produces an improvement in the cognitive abilities of the subject.

Embodiment 122: The method according to any one of embodiments 95-121, wherein said method produces an improvement in, a stabilization of, or a reduction in the rate of decline of the clinical dementia rating (CDR) of the subject.

Embodiment 123: The method according to any one of embodiments 95-122, wherein the subject is a human and said method produces a perceived improvement in quality of life by the human.

Embodiment 124: The method according to any one of embodiments 95-123, wherein said method further comprises administering to said subject a drug for the treatment of a cognitive disorder and/or Alzheimer's disease.

Embodiment 125: The method of embodiment 124, wherein said drug comprises a cholinesterase inhibitor.

Embodiment 126: The method of embodiment 124, wherein said drug comprises a drug selected from the group consisting of donepezil, galantamine, memantine, rivastigmine, and Memantine+donepezil.

Embodiment 127: A method of treating depression, short-term memory loss, of improving memory, of improving cognition, of improving sleep, and/or of improving athletic performance in a subject, said method comprising:
  exposing said subject to blinking blue light at a frequency ranging from about 20 Hz up to about 60 Hz, or from about 30 Hz up to about 50 Hz, or from about 35 Hz up to about 45 Hz, or at about 40 Hz, at an intensity and duration sufficient to mitigate a symptom, or slow or stop the progression of said neurodegenerative condition.

Embodiment 128: The method of embodiment 127, wherein said blue light comprises a blue light or a blue spectral component of a light in the wavelength range from about 440 nm up to about 495 nm, or from about 440 nm up to about 480 nm, or from about 450 nm up to about 480 nm, or from about 450 nm up to about 470 nm.

Embodiment 129: The method of embodiment 128, wherein the blue light or blue spectral component of a light has a maximum at about 460 nm.

Embodiment 130: The method according to any one of embodiments 128-129, wherein said blinking blue light is administered by a device according to any one of embodiments 1-92, or a system according to any one of embodiments 93-94.

Embodiment 131: A light therapy system, such as for treatment of Alzheimer's disease, depression, dementia, short-term memory, or for improved learning, improved athletic performance or improved cognitive performance, the light system comprising a blue light source that operates at a frequency in the range from 20 to 50 Hz (preferably around 40 Hz), whereby the system enables retinal ganglion cells of a human to be exposed in order to stimulate brain waves (gamma oscillations in the human's brain).

Embodiment 132: A light therapy system, such as for treatment of Alzheimer's disease, depression, dementia, short-term memory, or for improved learning, improved athletic performance or improved cognitive performance, the light system comprising a sleep mask that comprises a blue light source for illumination of a human's eye lids, said blue light operates at a frequency in the range from 20 to 50 Hz (preferably around 40 Hz), whereby the system enables retinal ganglion cells of a human wearing the mask to be exposed be a fraction of the emitted blue light (a fraction that penetrates though the eye lids) over a total time period of more than 1 hour in order to stimulate brain waves (gamma oscillations in the human's brain).

Embodiment 133: A light therapy system, such as for treatment of Alzheimer's disease, depression, dementia, short-term memory, or for improved learning, improved athletic performance or improved cognitive performance, the light system comprising comprises a narrow spectrum light source with a peak intensity in the blue part of the light spectrum, such as around 460 nm, and a broad spectrum light source covering a majority or all of the visible light spectrum, wherein the narrow spectrum light source is a stroboscopic blue light source that operates at a frequency in the range from 20 to 60 Hz (preferably around 40 Hz) and has a majority of its power within the wavelength range from 440 nm to 480 nm, the broad spectrum light source is a continuous light source that has a majority of its power outside the wavelength range from 440 nm to 480 nm, whereby the two light sources in combination provides a substantially white light illumination.

Embodiment 134: A light therapy system, such as for treatment of Alzheimer's disease, depression, dementia, short-term memory, or for improved learning, improved athletic performance or improved cognitive performance, the light system comprising comprises a first light source and a second light source, wherein the light sources operate at a frequency in the range from 20 to 60 Hz (preferably around 40 Hz) and are synchronized in a manner such that the combined light from the light sources are substantially constant in power.

Embodiment 135: A light therapy system according to embodiment 134, wherein said first light source has a spectral component around 460 nm that is larger than a spectral component of around 460 nm of said second light source.

Embodiment 136: A light therapy system according to any one of embodiments 131 to 135, wherein said light source(s) comprise LED-based light source(s).

Embodiment 137: A light therapy system according to any one of embodiments 131-136, wherein said first light source comprises the wavelengths 460 nm, 650 nm, and 570 nm, and a second light source comprises the wavelengths 490 nm, 770 nm and 600nm.

Embodiment 138: A method of treating of Alzheimer's disease, depression, dementia, and/or improving short-term memory, and/or improving learning, and/or improving athletic performance, and/or improving cognitive performance in a mammal, said method comprising:
  exposing said mammal to a light source comprising an oscillating blue light that operates at a frequency ranging from about 20 Hz to about 50 Hz.

Embodiment 139: A method of using a light therapy system according to any of the embodiments 131-137, wherein the system is used by an individual (for example a patient, a prisoner, a student, an elderly individual in a private home, or an athlete) for optimizing rehabilitation, recovery, physiotherapy, practice, training and/or performance at competition.

Definitions

The terms "subject," "individual," and "patient" may be used interchangeably herein and typically refer to a mammal, in certain embodiments a human or a non-human primate. While the phototherapy devices and systems described herein are described with respect to use in humans, they are also suitable for animal, e.g., veterinary use. Thus, certain illustrative organisms include, but are not limited to humans, non-human primates, canines, equines, felines, porcines, ungulates, lagomorphs, and the like. Accordingly, certain embodiments contemplate use of the phototherapy devices and systems described herein with domesticated mammals (e.g., canine, feline, equine), laboratory mammals (e.g., mouse, rat, rabbit, hamster, guinea pig), and agricultural mammals (e.g., equine, bovine, porcine, ovine), and the like. The term "subject" does not require one to have any particular status with respect to a hospital, clinic, or research facility (e.g., as an admitted patient, a study participant, or the like). Accordingly, in various embodiments, the subject can be a human (e.g., adult male, adult female, adolescent male, adolescent female, male child, female child) under the care of a physician or other health worker in a hospital, psychiatric care facility, as an outpatient, or other, clinical context. In certain embodiments, the subject may not be under the care or prescription of a physician, or other, health worker. In certain embodiments the subject may not be under the care a physician or health worker and, in certain embodiments, may self-prescribe and/or self-administer a phototherapy regimen using, e.g., the devices and/or systems described herein.

The terms "treatment," "treating," or "treat" as used herein, refer to actions that produce a desirable effect on the symptoms or pathology of a disease or condition, particularly those that can be effected utilizing the phototherapy devices and phototherapy regimen described herein, and may include, but are not limited to, even minimal changes or improvements in one or more measurable markers of the disease or condition being treated. Treatments also refers to delaying the onset of, retarding or reversing the progress of, reducing the severity of, or alleviating or preventing either the disease or condition to which the term applies, or one or more symptoms of such disease or condition. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

The terms "Planckian locus" or "black body locus" or "$D_{UV}$" are used interchangeably and refer to the path or locus that the color of an incandescent black body would take in a particular chromaticity space as the blackbody temperature changes. It goes from deep red at low temperatures through orange, yellowish white, white, and finally bluish white at very high temperatures.

A color space is a three-dimensional space; that is, a color is specified by a set of three numbers (the CIE coordinates X, Y, and Z, for example, or other values such as hue, colorfulness, and luminance) which specify the color and brightness of a particular homogeneous visual stimulus. A chromaticity is a color projected into a two-dimensional space that ignores brightness. For example, the standard CIE XYZ color space projects directly to the corresponding chromaticity space specified by the two chromaticity coordinates known as x and y, making the familiar chromaticity diagram shown in the figure. The Planckian locus, the path that the color of a black body takes as the blackbody temperature changes, is often shown in this standard chromaticity space.

The "color temperature" of a light source is the temperature of an ideal black-body radiator that radiates light of a color comparable to that of the light source. Color temperature is conventionally expressed in kelvin, using the symbol K, a unit of measure for absolute temperature.

A "spectral component" of a light source indicates that the light produced by the light source comprises light within a particular referenced wavelength range. Approximate wavelength and frequency ranges for various colors are shown in Table 1, and when colors or spectral components are referenced with respect to colors the light consists or comprises illumination within the recited ranges.

TABLE 1

Approximate wavelength and frequency ranges for various colors.

| Color | Wavelength | Frequency |
|---|---|---|
| violet | 380-450 nm | 668-789 THz |
| blue | 450-495 nm | 606-668 THz |
| green | 495-570 nm | 526-606 THz |
| yellow | 570-590 nm | 508-526 THz |
| orange | 590-620 nm | 484-508 THz |
| red | 620-750 nm | 400-484 THz |

Thus, for example, a light source having or comprising a blue spectral component emits illumination at least a portion of which falls within the 450 nm to 495 nm wavelength range. A light source consisting of a blue spectral component emit illumination all of which falls within the 450 nm to 495 nm wavelength range.

The terms "flickering" or "blinking", or "stroboscopic" when used herein with respect to a light source or a component of a light source indicates that the light source or the component of the light source alternates between two different brightness states (e.g., a high state and a low state) in at least one spectral component. In certain embodiments the light source, or alternates between a high state and a low state in all spectral components emitted by the light, although the brightness/intensity of the high and low state may differ in different spectral components. In certain embodiments the light source alternates between two different brightness states in all visible spectral components of the light source. In certain embodiments the light source alternates between an on state and an off state. In certain embodiments the light source, or a spectral component thereof, alternates between a "high" illumination state (e.g., full on/brightness) and a lower illumination state. In certain embodiments the lower state has a brightness that is about 75% or less, or about 70% or less, or about 60% or less, or about 50% or less, or about 40% or less, or about 30% or less, or about 20% or less, or about 10% or less, or about 5% or less, or about 3% or less, or about 1% or less, than the high state in at least one spectral component.

The "duration of a blink" refers to the time duration between the lowest illumination state and the next following lowest illumination state.

That a spectral component produced by a second light source is less than a spectral component produced by a first light source indicates that the luminance produced by the referenced spectral component in the second light source is less than the luminance produced by the spectral component in the first light source. In certain embodiments this is measured as the luminance at the wavelength of maximum intensity produced by the lamp(s) providing that spectral component. In certain embodiments this is measured as the luminance integrated across the full wavelength range of the spectral component at issue. In certain embodiments the second light source luminance in the spectral component(s) at issue is less than about 60%, or less than about 50%, or less than about 40%, or less than about 30%, or less than about 20%, or less than about 10%, or less than about 5%, or less than about 3%, or less than about 2%, or less than about 1%. In certain embodiments the second light source provides no illumination in the spectral component of interest.

The "critical flicker fusion frequency", "flicker fusion threshold", or "flicker fusion rate" refers to a concept in the psychophysics of vision. It is defined as the frequency at which an intermittent (e.g., blinking) light stimulus appears to be completely steady to the average human observer. Flicker fusion threshold is related to persistence of vision The phrase "source is substantially undetectable by human vision" when used with respect to a flickering or blinking light means that a human illuminated by or observing the illumination cannot see the blinking component of the light and instead perceives the illumination as substantially constant, even where the frequency of the blinking light/light component is below the flicker fusion threshold. The critical fusion frequency depends on the luminance of the stimulus and its size (see, e.g., Hecht and Smith (1936) *J. Gen. Physiol.* 19(6): 979-89). For a large, high luminance stimulus covering the fovea, like a full screen white field on a CRT, flicker fusion occurs at about 60 Hz.

The terms "light source" and "illumination source" are used interchangeably and refer to a device that provides light typically within the visible spectrum for humans. The light source can comprise one or a plurality of lamps and can deliver light comprising, or consisting of, specific spectral components.

The terms "lamp" or "bulb" are used interchangeably and refer to device that creates light, typically by the application of electricity. A lamp includes, but is not limited to light emitting diode (LED), a laser, a tungsten bulb (that may be filtered to provide specific spectral component(s)), a halogen bulb (that may be filtered to provide specific spectral component(s)), a xenon bulb (that may be filtered to provide specific spectral component(s)), and the like.

When referring to the difference in illumination angel between the first light source and the second light source determined with respect to the center ray produced by the light source. In certain embodiments the difference in illumination angle refers to the illumination angle of the light as it passes from the phototherapy device rather than from the first or second light source. Accordingly, where the phototherapy device comprises a diffuser or collimator, the difference in illumination angle between the first light source and second light source is identical.

A "duty cycle" is the fraction of one period in which a signal or system is active. Duty cycle is commonly expressed as a percentage or a ratio. Thus, a 60% duty cycle means the signal (e.g., light source) is on 60% of the time but off 40% of the time.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 schematically shows one illustrative, but non-limiting embodiment of a phototherapy device described herein. As illustrated the device 100 comprises a first light source 101 comprising lamps 103, 104, and 105, a second light source 102 comprising lamps 106 and 107, a diffuser 108, a controller 110 comprising controls for one or more of on/off and/or brightness 112, blink frequency 113, phase and/or duty cycle 114, color temperature and/or hue 115, and the like.

FIG. 6, panel B shows an illustrative, but non-limiting chromaticity diagram for the second light source (e.g., LED2).

DETAILED DESCRIPTION

Figure 1:
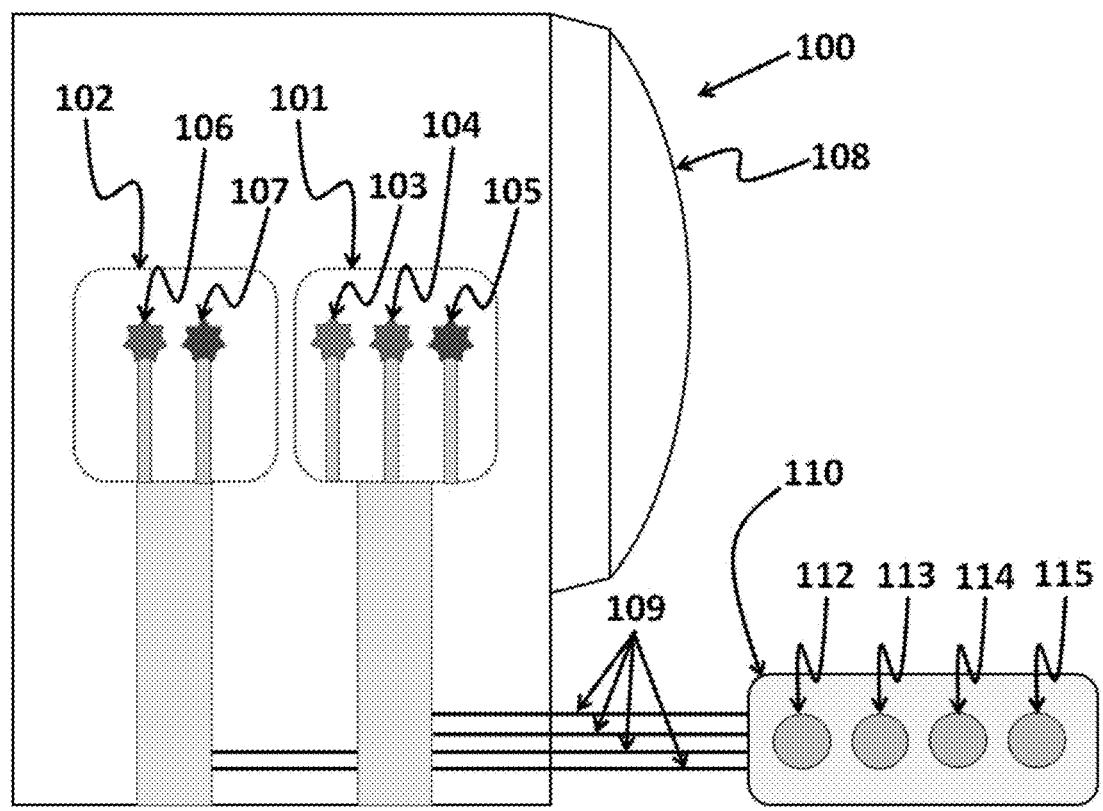

New studies have shown that flickering light at 40 hertz can reduce the beta amyloid plaque production (early clinical signs of Alzheimer's) in an Alzheimer's Disease (AD) mouse model by stimulating the brain wave activity (e.g., gamma oscillations) in the visual cortex (see, e.g., Iaccarino et al. (2016) *Nature*, 540(7632): 2300. However, trials on mice cannot be duplicated in humans due to the negative side effects of flickering light, essentially hampering the opportunity to pursue this methodology in clinical trials.

In particular, flickering light applied to humans has been observed to induce convulsions (e.g., in epileptics or subject prone to epilepsy), to induce headaches, to cause visual fatigue, to inhibit focus and/or attention, to create feelings of ocular discomfort and/or emotional discomfort, to provide undesirable glare. It is also known that blinking light at certain frequencies induces stress in humans and non-human mammals. These adverse effects, while perhaps tolerable in certain subjects for very short time intervals, are believed to prohibit the therapeutic application of flickering light regimes to humans over prolonged time intervals (e.g., greater than about 10 minutes, or greater than about 15 minutes, or greater than about 30 minutes, or greater than about 45 minutes, or greater than about 1 hour, or greater than about 1.5 hours, or greater than about 2 hours, or greater than about 2.5 hours, or greater than about 3 hours).

In various embodiments phototherapy devices are provided that deliver a blinking illumination effective to induce or entrain brain oscillations (e.g., gamma oscillations) and thereby mitigate or prevent various neurodegenerative conditions including but not limited to Alzheimer's disease, mild cognitive impairment (MCI), dementia, and the like. The phototherapy devices are designed so that the blinking light is generally imperceptible by the subject (e.g., a human) which remaining effective to induce and/or to entrain the brain oscillations. As the blinking cannot be observed by the subject, it is believed the adverse effects of blinking light referenced above can substantially be avoided providing for effective and prolonged phototherapy treatments.

Without being bound by a particular theory it is believed that the phototherapy systems and devices described herein find utility in the prevention and/or treatment of various neurodegenerative conditions including, but not limited to Alzheimer's disease (AD), dementia, mild cognitive impairment (MCI) and the like. This has important implications for public health.

One of the biggest demographic challenges in Europe and the US is the rapidly growing number of people with Alzheimer's and dementia (~30% of the world population has or will develop the neurodegenerative disease). Dementia is one of the leading causes of death among those 60 years and over. The increase in the number of Europeans and Americans living with dementia is already creating immense challenges for the health and socioeconomic systems and will cost the US nation more than 250 billion dollars in healthcare. For most people, the cognitive decline starts with a failing memory and a lack of perception and attention.

It is important to notice that Alzheimer's and dementia are practically untreatable today. Despite decades of scientific and pharmaceutical research, patients are left without any hope of recovery and reversal of the disease and at best current available treatment can alleviate the symptoms and only slightly slow down disease progression.

It is believed the phototherapy devices and systems described herein can be used to or the treatment and/or prophylaxis of the neurodegenerative brain disease chronic traumatic encephalopathy (CTE) which has been associated with Alzheimer's-like symptoms and is experienced by athletes who has suffered repeated head traumas (series of concussions). Recent years have uncovered severe problems in the sports area for American football players, with widespread problems in their post-career with memory loss, confusion, aggression, rage and, at times, suicidal behaviour.

Related to the above, sleep-deprived living, such as stressful lives, night-shift working, and hormone-disturbing substances, are adding to the growth of neurological disorders. Scientific studies have showed a clear relation between sleep-deprivation and the onset of Alzheimer's and dementia. As an example, surgeons (having 24 hour shifts) develop Alzheimer's around 10 years earlier than the general population. Similar results are known for shift-workers and people with frequent exposure to jet-lag, and concerns extend to busy business people. The root cause of this is that during sleep, the brain naturally reduces toxic proteins that otherwise develop into plague and cause death of neurons that again leads to Alzheimer's and dementia.

Accordingly phototherapy systems and devices are provided herein that are believed to be effective to induce and/or entrain brain oscillations (e.g., gamma oscillations) and thereby function in the prophylaxis and/or treatment of various neurological disorders. Additionally, methods of use of these devices and systems are provided.

Phototherapy Device

It was discovered that it is possible to provide a therapeutic lamp (or lamp system) (a phototherapy device) that modulates the neuron responses in different parts of the brain (such as the hippocampus) without substantially affecting the vision of the subject (see, e.g. FIG. 1). In particular embodiments, the phototherapy device provides a blinking light effective to induce or entrain brain oscillations (e.g., gamma oscillations) and thereby improve cognition and/or prevent or mitigate a neurodegenerative disorder. It was discovered in studies investigating the brain response to blue and green light sources using functional nuclear magnetic resonance imaging that the activity of the hippocampus is significantly increased in response to blue light as compared to green light (see, e.g., Vandewalle et al. (2010) *Proc. Natl. Acad. Sci. USA*, 107: 19549-19554; and the like).

Exploiting this discovery, a phototherapy device was developed that utilizes multiple wavelengths of illumination. In certain embodiments, particular wavelengths (e.g., spectral components) are selected to stimulate or entrain brain activity by administering them at a time varying intensity (e.g., blinking), while other wavelengths are utilized to mitigate adverse effects of the time-varying stimulation. One advantage, inter alia, of using multiple wavelengths in the device is that the brain response depends on the specific wavelengths and this wavelength dependence is different from the wavelength sensitivity of the eye vision. The wavelength sensitivity of the receptors at the retina human (and other mammalian) vision is different from the wavelength sensitivity of the receptors (non-visual ganglion cells) that controls hormone activity and the activity in the brain (e.g., hippocampus).

The present inventors have therefore realized that it is possible to develop a phototherapy device where modulation of the neuronal response in the brain is obtained without substantially affecting the vision. The system therefore provides an experience by a human's (or other mammal's) brain activity is modulated, but subject will not see the blinking/stroboscopic effect.

Figure 3:
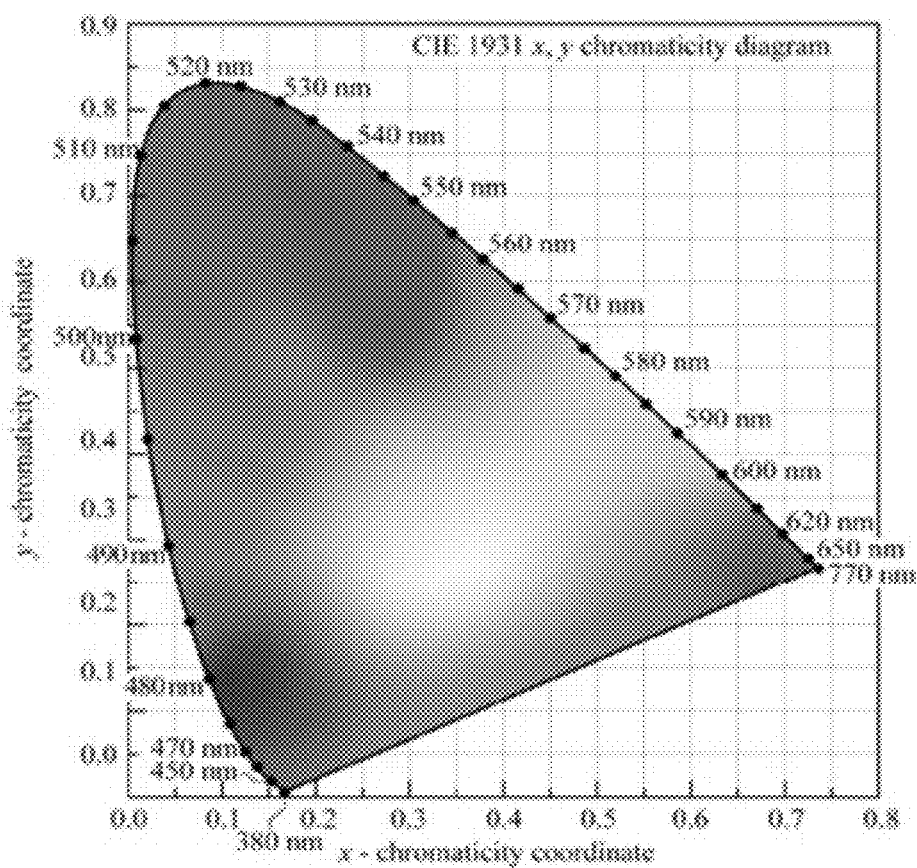
FIG. 3 shows a chromaticity diagram illustrating how a specific white light color can generated with different wavelengths combinations FIG. 4A schematically illustrates one embodiment of the modulation of two light sources for a light therapy device described herein where light is modulated between a full-on and an off state.
Figure 6:
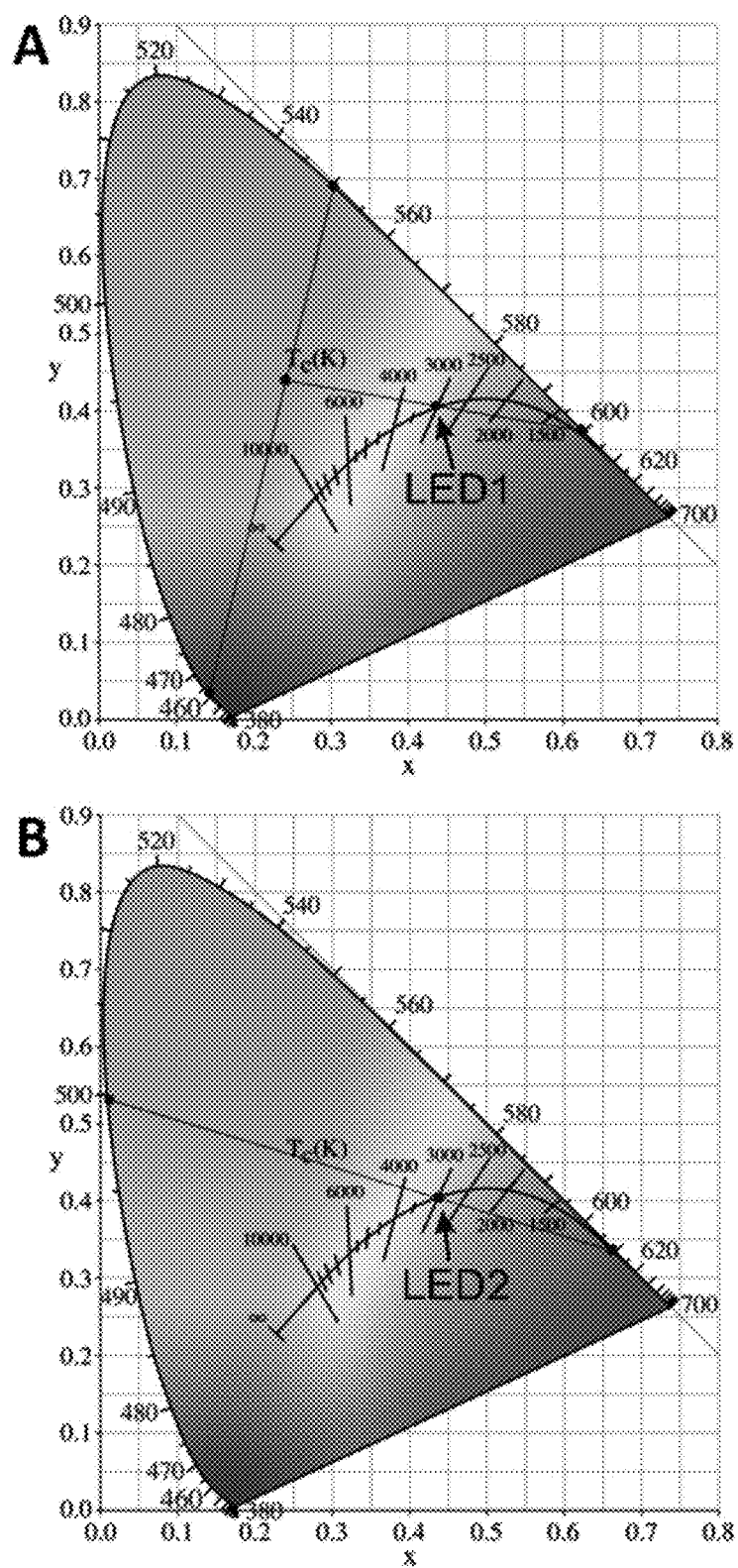
FIG. 6, panel A, shows an illustrative, but non-limiting chromaticity diagram for the first light source (e.g. LED1). In this illustration, the light source consists the colors with wavelengths 460 nm, 550 nm, and 600 nm.

In certain embodiments this is accomplished by a phototherapy device comprising at least two providing two light sources. A first light source contains a blue light component" and the light source blinks at a frequency and intensity that induces or entrains brain oscillations in a mammal. A second light source is provided that lack the blue component t or that contains the blue component at a substantially lower level than the blue component is the first light source. Despite the different spectral composition of the first light source and the second light source, the spectral components are selected so that the illumination produced by the first light source and the second light source are substantially indistinguishable (e.g., in color) to the human (or other mammalian subject's) vision. FIGS. 3 and 6 show typical chromaticity diagrams illustrating how a specific light color (e.g., white light) can generated with different wavelengths combinations. Typically, both the first and second light source will appear "white" although it will be recognized, and apparent from the chromaticity diagrams, that the light sources can be operated to provide other colors.

Since at least the blue component of the first light source is blinking, and typically the entire first light source is blinking, to render the blinking substantially undetectable, the second light source is operated in a blinking mode so it compensates for intensity changes in the first light source. Thus, for example, when the first light source decreases in intensity, the second light source provides a corresponding increase in intensity. Conversely, when the first light source increases in intensity, the second light source provides a corresponding decrease in intensity. The result is that a blinking blue spectral component is produced while the combined illumination (first and second light source) appears substantially constant in intensity and color.

Accordingly, in various embodiments a phototherapy device is provided that delivers a blinking (flickering) illumination at a therapeutic intensity and wavelength (e.g., blue light component) where the blinking is substantially undetectable by human vision even where the blink frequency is below the flicker fusion threshold. One such device is illustrated schematically in FIG. 1. As illustrated therein the phototherapy device 100 comprises a first light source 101 that produces a light that comprises or consists of a blue spectral component where at least the blue spectral component (and all the illumination produced by the first light source) is provided as a blinking light. The phototherapy device also typically comprises a second source 102 that produces a light either substantially lacking a blue spectral component (e.g., substantially lacking a light component in the range of about 450 nm to about 495 nm) or, where the second light produces a blue spectral component, the blue spectral component produced by the second light source is smaller than the blue spectral component of the light produced by the first light source. Typically, the illumination produced by the second light source supplements the illumination produced by the first light source so that the blinking of the first light source when combined with the light from said second light source is substantially undetectable by human vision, even where the blinking frequency is below the flicker fusion rate (e.g., below about 60 Hz).

In certain embodiments the blinking frequency and intensity of the first light source is sufficient to stimulate or to entrain brain waves in a human's brain when the human is exposed to said light source. In certain embodiments the stimulated or entrained brain waves comprise gamma oscillations.

A "gamma wave" or "gamma oscillation" is a pattern of neural oscillation in humans with a frequency between about 25 and about 100 Hz (Hughes (2008) *Epilepsy Behav.* 13(1): 25-31), though 40 Hz is typical (Gold (1999) *Consciousness and Cognition,* 8(2): 186-195). Gamma waves can be observed as neural synchrony from visual cues in both conscious and subliminal stimuli (see, e.g., Melloni et al. (2007) *J. Neurosci.* 27(11): 2858-2865; Siegel et al. (2008) *Neuron,* 60(4): 709-719; Gregoriou et al. (2009) *Science,* 324(5931): 1207-1210; Baldauf et al. (2014) *Science,* 344 (6182): 424-427; and the like). Gamma waves are also implicated during rapid eye movement sleep and anesthesia, which involves visualizations (see, e.g., Vanderwolf (2000) *Brain Res.* 855(2): 217-224).

Figure 2:
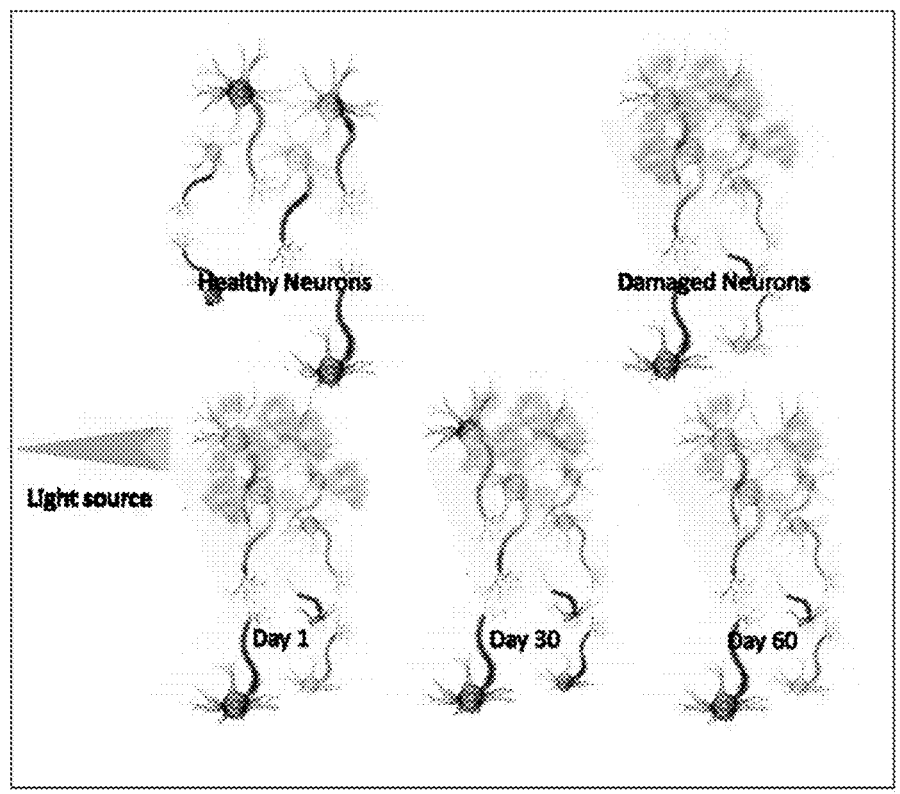
FIG. 2 schematically illustrates the use of a blue light therapy system with a blue stroboscopic light that stimulates neural activity to decrease amyloid plague formation in the brain.

Without being bound to a particular theory, it is believed that provision of an appropriate blinking light can synchronize neuron activity and it is believe this is beneficial to people with dementia or Alzheimer since the neuron activity will improve and lead to better memory and coordination of human activities. More specifically, it is believed the use of blinking illumination for the induction or entrainment of gamma oscillations can attenuates amyloid load and/or modify microglia in the brain of a mammal. Accordingly, it is believed the blinking light produced by the phototherapy devices described herein can find utility in in the treatment and/or prevention of Alzheimer's disease, dementia, mild cognitive impairment (MCI), and related conditions. In this regard, FIG. 2 shows schematically how a phototherapy device or system, as described herein can use a blinking light source to stimulate neural activity to decrease amyloid plaque formation in the brain. The light therapy system provides light exposure to the ganglia cells in the eyes of a patient to stimulate brain waves, so-called gamma oscillations, in a manner in which the person is largely undisturbed by the stroboscopic effect.

As noted above, in certain embodiments, the phototherapy devices use two (or more) light sources comprising different wavelengths, where a first light sources acts to stimulate the brain via stroboscopic (blinking) blue light or blue light component, and where a second light sources acts to supplement the first light source in such a manner that a human being exposed to the combined light from the two sources does not experience visual disadvantages by the stroboscopic (blinking) effect. As noted above, in certain embodiments the illumination produced by the second light source supplements the illumination produced by the first light source so that the blinking of the first light source when combined with the light from said second light source is substantially undetectable by human vision, even where the blinking frequency is below the flicker fusion rate (e.g., below about 60 Hz).

More particularly, in certain embodiments, the phototherapy device comprises two light sources (e.g., two LED systems), a first light source and a second light source, (light sources 1 and 2, respectively), that have almost the same color temperatures. Typically, the first light source comprises or consists of a blue spectral component, produced, for example, by a blue lamp (103 in FIG. 1), and at least the blue spectral component is a blinking component. In certain embodiments all the illumination produced by the first light source is a blinking illumination.

In certain embodiments the first light source produces light that comprises or consists of a blue spectral component, a green spectral component, and an orange and/or red spectral component. In certain embodiments the first light source comprises or consists of a lamp that emits primarily a blue light (103 in in the embodiment illustrated in FIG. 1), a lamp that emits primarily a green light (104 in in the embodiment illustrated in FIG. 1), and a lamp that emits primarily an orange and/or red light (105 in in the embodiment illustrated in FIG. 1). Any of a number of lamps are suitable, however in certain embodiments the lamps comprise one or more LEDs.

FIG. 6, panel A, shows a chromaticity diagram for an illustrative embodiment for the first light source. As shown, the first light source has three colors with wavelengths (e.g., wavelength maxima) at 460 nm, 550 nm, and 600 nm. The color coordinates are shown in the chromaticity diagram in FIG. 6, panel A. As illustrated therein, the color mixing of the three colors leads to a white light source similar to a black body radiator with a color temperature of about 3000 K. This in indicated by the black arrow in FIG. 6, panel A. In one illustrative, but non-limiting embodiment see, e.g., FIG. 1) this can be achieved by providing three different lamps (e.g., LEDs) in the first light source: One lamp 103 that produces a blue spectral component, one lamp 104 that produces a green spectral component, and one lamp 105 that produces a red and/or orange spectral component. It is noted that, while the first light source 101 is shown in FIG. 1 as containing three lamps, it will be recognized the first light source and comprise or consist of more or fewer lamps. For example, multiple (e.g., 2, 3, 4, or more) lamps 103 can be used to generate a blue spectral component, and/or multiple (e.g., 2, 3, 4, or more) lamps 104 can be used to generate a green spectral component, and/or multiple (e.g., 2, 3, 4, or more) lamps 105 can be used to generate an orange/red spectral component. Thus, as desired, in certain embodiments, multiple lamps can be used to increase the intensity of a particular spectral component. In certain embodiments two (or more) spectral components can be produced by a single lamp or by multiple copies of a single lamp.

The second light source produces a light lacking a blue spectral component or produces a blue spectral component that is smaller than the blue spectral component of the light produced by the first light source. In certain embodiments the second light source produces light that comprises or consists of a blue/green spectral component, an orange spectral component, and a red/far red spectral component, or the second light source produces light that completely lacks a blue spectral component (e.g., that consists essentially of a green spectral component, and an orange/red spectral component).

In certain embodiments, as illustrated in 6, panel B, the second light source can provide a light that is substantially lacking a blue spectral component. In the embodiments illustrated in FIG. 1, and FIG. 6, panel B, the second light source produces a light that consists (or consists essentially of green spectral component and an orange/red spectral component).

In certain embodiments the second light source comprises or consists of a lamp (e.g., 106 in FIG. 1) that emits primarily a green light (e.g. that produces primarily a green spectral component), and a lamp e.g., 107 in FIG. 1) that emits primarily an orange and/or red light. It is noted that, while the second light source 102 is shown in FIG. 1 as containing two lamps, it will be recognized the second light source can comprise or consist of more or fewer lamps. For example, multiple (e.g., 2, 3, 4, or more) lamps 106 can be used to generate a green spectral component, and/or multiple (e.g., 2, 3, 4, or more) lamps 107 can be used to generate an orange and/or red spectral component. Thus, as desired, in certain embodiments, multiple lamps can be used to increase the intensity of a particular spectral component. In certain embodiments two (or more) spectral components can be produced by a single lamp or by multiple copies of a single lamp.

Any of a number of lamps are suitable for use in the first light source and/or second light source. However, in various typical embodiments the lamps comprise one or more LEDs.

In the embodiment illustrated in FIG. 1, and FIG. 6, panel B, the second light source comprise two lamps (e.g., 2 LEDs) providing two spectral components. Thus, the second light source can comprise LED(s) that emit at 500 nm and 610 nm, respectively, and the lamp will emit white light with a color temperature of 300 K+$\Delta$T (see, e.g., FIG. 6, panel B). Looking directly into the two lamps with the human eye, the two lamps LED1 and LED2 will appear identical, or almost identical, if the following four conditions are fulfilled:

1) The difference in correlated color temperatures $\Delta$T between the first light source and the second light source is small (e.g., about 50K or less or about 30K, or about 20K or less, or about 10K or less, or about 5K or less, or in certain embodiments ranges from about 0.5K, or from about 1K or from about 5K up to about 10K);
2) For each light source (light source 1 and light source 2) the distance to the black-body locus $D_{UV}$ is small (e.g., less than about 0.01, or less than about 0.001, or less than about 0.0001);
3) The first light source and the second light source provide illumination at approximately the same lux level (e.g., the difference in intensity between the first light source and the second light source is less than about 100 lux, or less than about 75 lux, or less than about 50 lux, or less than about 40 lux, or less than about 30 lux, or less than about 20 lux, or less than about 10 lux, or less than about 5 lux, or less than about 2 lux); and
4) The first light source and the second light source emit light in substantially the same direction (e.g., the difference in illumination angel between the first light source and the second light source is less than about 30 degrees, or less than about 25 degrees, or less than about 20 degrees, or less than about 15 degrees, or less than about 10 degrees, or less than about 5 degrees, about 1 degree or less).

In the example illustrated by FIG. 6, light source 1 (first light source) and light source 2 (second light source) consist of three and two colors. However, in general both light sources lamps can consist of many colors (more than 3 or 2). However, for maximum efficacy, it is desired that $\Delta$T be kept small and that that $D_{uv}$ for each lamp is small.

In another illustrative, but non-limiting embodiment, the first light source is an LED based light source (e.g., lamp) that comprises the wavelengths 460 nm (blue spectral component), 570 nm (green spectral component), and 650 nm (red spectral component), and the second light source (e.g., lamp) is an LED based light source that comprises the wavelengths 490 nm (blue spectral component), 770 nm (far red spectral component) (or 670 nm (red spectral component)) and 600 nm (orange spectral component).

As noted above, lamps that provide various spectral components in the first and/or second light source can comprise multiple lamps that contribute to a particular spectral component. It will be recognized that in certain embodiments, multiple lamps with different wavelength profiles may contribute to a "single" spectral component. Thus, for example, a blue spectral component can be produced by the combination of one lamp having a maximum emission at a wavelength of 460 nm and a second lamp having a maximum emission at a wavelength of 480 nm. This is illustrative and non-limiting. Using the teaching provided herein, one of skill in the art can routinely utilize one or more lamps to provide light sources suitable for use in the phototherapy devices described herein.

Figure 4A:
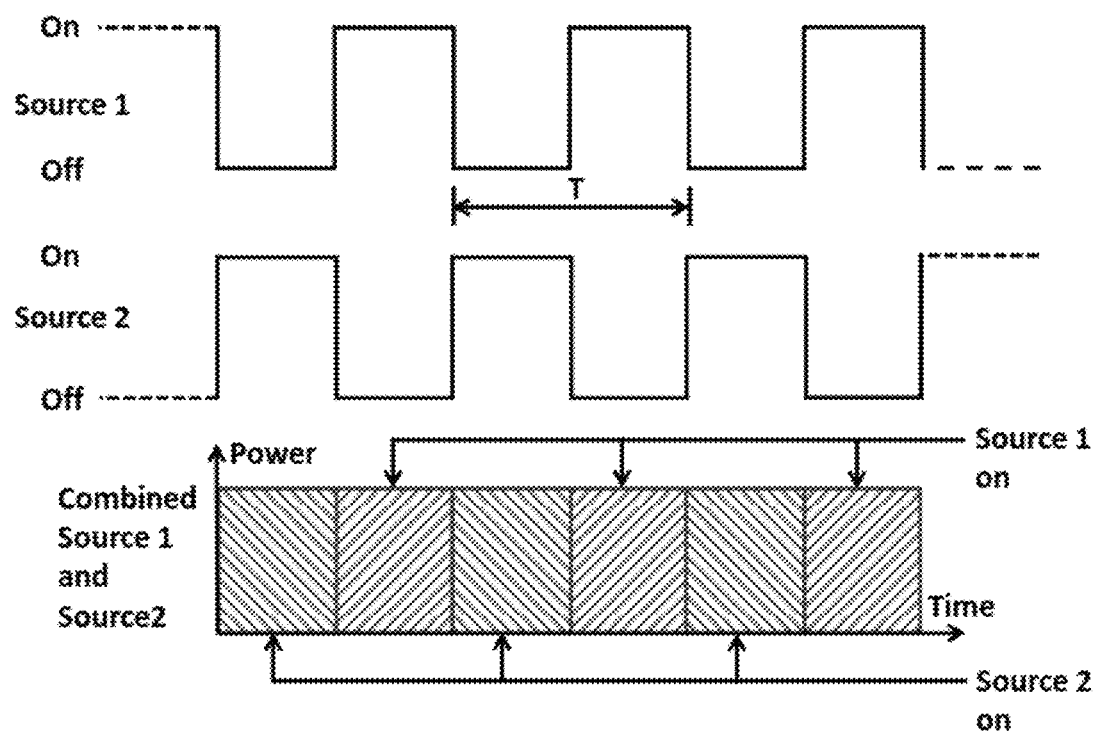
FIG. 4B schematically illustrates one embodiment of the modulation of two light sources for a light therapy device described herein where light is modulated between a high state (e.g., full-on) and a low, but non-zero (not off) state.
Figure 7:
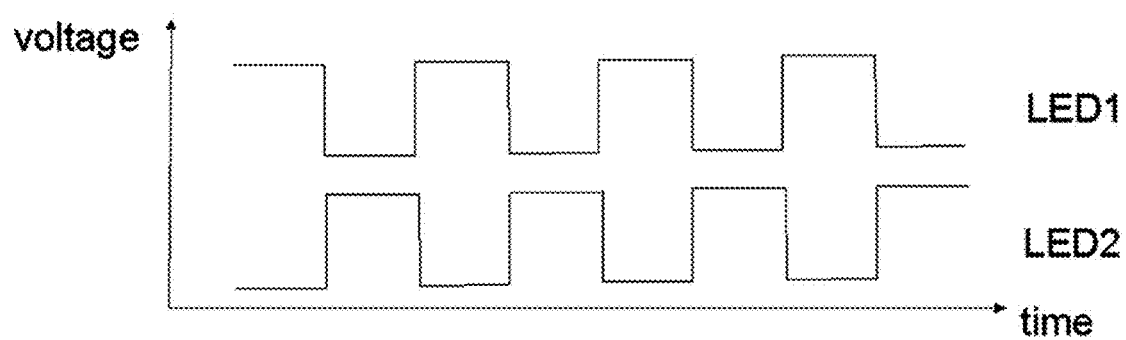
FIG. 7 illustrates one embodiments of the power supply voltage for the two light sources (first light source and second light source). In this illustrative, but non-limiting embodiment, the voltages are 180 degrees out of phase. The combination of light produced by the first light source and the second light source results in a continuous substantially constant illumination.

The changes in intensity (and/or spectral composition) of the two light sources (first light source and second light source) are substantially synchronized/coordinated such that intensity changes (and/or visible color changes) in the first light source are compensated for by intensity changes (and/or visible color changes) in the second light source to provide a combined illumination that is substantially constant (e.g., flicker-free). Thus, as illustrated in FIG. 4A, which shows a schematic illustration of the alternating combination of the two light sources, the light sources are modulated on-off 180 degrees out of phase so that when the first light source is on, the second light source is off. This is also illustrated by the power supply voltage for the two light sources, e.g., LED1 and LED2 shown in FIG. 7. Again, the two voltages are 180 degrees out of phase and therefore, when one of the light sources is "on" the other light source is "off". When the above four above conditions are fulfilled the two light sources have the same visual appearance and when the lamps compensate for each other's blinking, e.g., as explained above, the blinking will not be visible for the human eye when illuminated by or looking into the phototherapy device.

Accordingly, in certain embodiments the light sources (first light source and second light source) are operated out of phase so that illumination provided by the second light source corrects for changes in illumination provided by the first light source thereby providing illumination that appears substantially constant to a subject (e.g., to a human or to a non-human mammal) even at a blink rate below the flicker fusion frequency for the subject.

Figure 4B:
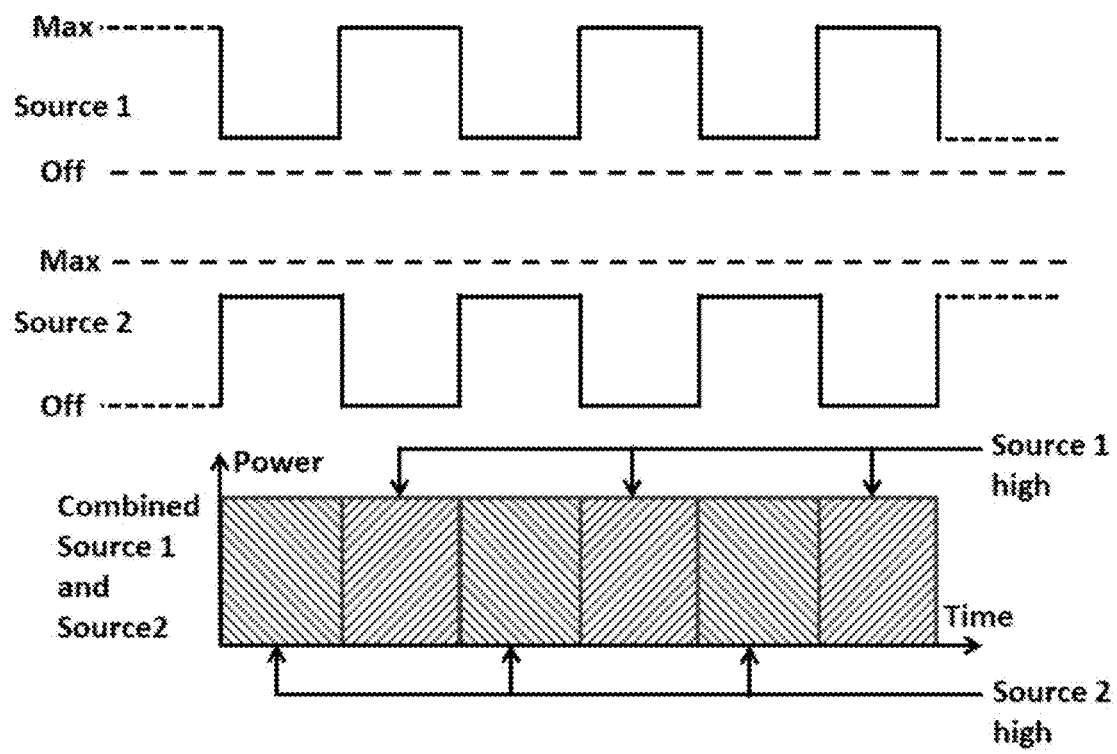
Figure 5:
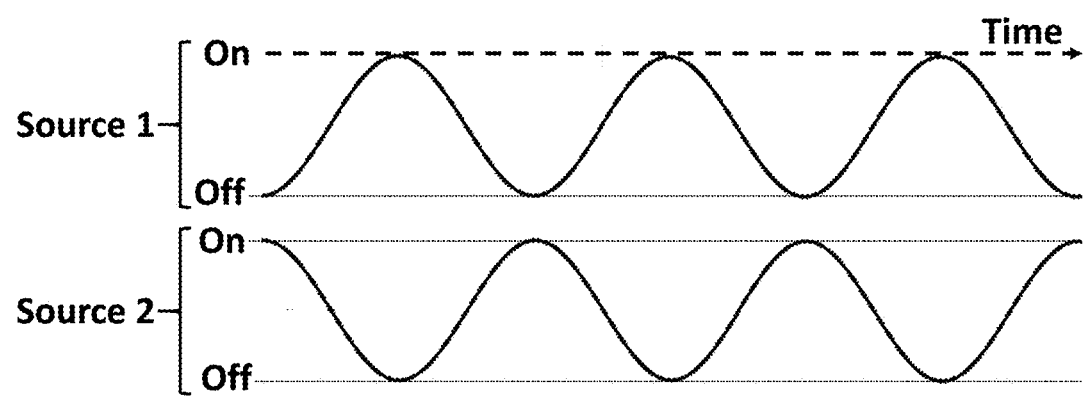
FIG. 5 shows another schematic illustration of the modulation of two alternating light sources in a sinusoidal pattern.

In the illustrative examples shown in FIGS. 4A, 4B, and 6 the light sources are modulated on-off (or high-low) and are essentially driven by a square wave voltage source. However, it will be recognized that the first light source and the second light source can be ramped up and down in gradual linear or non-linear manner. Thus, for example, FIG. 5 shows another schematic illustration of alternating light sources, where the light sources are modulated in a sinusoidal form. Accordingly, there are periods where the light sources are emitting radiation at the same time, although at respective levels (at any given time) to produce a constant total illumination. In both examples, the total power emitted from the combination of light sources is substantially uniform over time. Hence, the experience by a human is constant white light illumination, but the white light is composed of two different light sources of which one provides substantially more light, e.g., from 440 nm to 480 nm to the non-visual ganglion cells at the retina and therefore increased brain activity via stroboscopic light around 460 nm. It will be recognized that other wave forms for the illumination can be used. Such wave forms include, but are not limited to triangle, sawtooth, various non-linear waveforms, and the like.

Particular in view of the various possible waveforms that can be used to for the first and second light sources, the two sources need not necessarily operate 180 degrees out of phase. Accordingly, in certain embodiments, the phase difference between the first light source and the second light source ranges from about 45 degrees, or from about 60 degrees, or from about 75 degrees, or from about 90 degrees up to about 180 degrees, or up to about 165 degrees, or up to about 150 degrees, or up to about 135 degrees. In certain embodiments the phase difference between the first light source and the second light source is about 180 degrees so that when the first light source is on, the second light source is off and vice versa.

FIGS. 4A, 4B, and 6 illustrate the first light source and the second light source operating at a duty cycle of about 50%. Thus, for example, in one illustrative, but non-limiting embodiments the phototherapy device uses an alternating combination of the light sources, at a 50% duty cycle at 40 HZ. Thus, the first light source comprising a blue spectral component (e.g., a 460 nm light) is stroboscopic at 40 HZ and the second light source (e.g., that does not comprise light at 460 nm) is stroboscopic at 40 HZ. The two light sources are substantially synchronized such that when the first light source is turned on, the second light source is turned off, and vice versa.

However, alternative duty cycles are also contemplated. In certain embodiments the duty cycle of the first light source and/or the second light source ranges from about 5% up, or from about 10%, or from about 15%, or from about 20%, or from about 25%, or from about 30%, or from about 35%, or from about 40% up to about 90%, or up to about 85%, or up to about 80%, or up to about 75%, or up to about 70%, or up to about 65%, or up to about 60%. In certain embodiments the duty cycles of the first light source and the second light source are the same (e.g., in certain embodiments both light sources operate with a 50% duty cycle or one of the other duty cycles identified above). However, in other embodiments the first light source and the second light source have different duty cycles. Thus, for example, in certain embodiments the duty cycle of the first light source is 10% and the duty cycle of the second light source is 90% (e.g., a duty cycle ratio of 10:90). Other duty cycle rations contemplated include, but are not limited to 5:95, 25:75, 75:25, 95:5, and the like. In certain embodiments the ratio of duty cycle of the first light source to the second light source ranges from about 1:10 to about 10:1, or from about 1:5 to about 5:1, or from about 1:2 to about 2:1, or is about 1:1.

As noted above, in various embodiments the blue spectral component of the second light source is lower than the blue spectral component of the first light source. In certain embodiments this is measured as the luminance at the wavelength of maximum intensity in the wavelength range from about 450 nm to about 495 nm. In certain embodiments this is measured as the luminance integrated across the wavelength range from about 450 nm to about 495 nm. In certain embodiments the second light source luminance in the blue spectral component is less than about 60%, or less than about 50%, or less than about 40%, or less than about 30%, or less than about 20%, or less than about 10%, or less than about 5%, or less than about 3%, or less than about 2%, or less than about 1% than the luminance in the blue spectral component produced by the first light source. In certain embodiments the second light source provides no illumination in the blue spectral component (e.g., from about 450 nm to about 495 nm).

It will be recognized by one of skill in the art that blinking of a spectral comment of the light or blinking of an entire light source need not be an alternation between a full-on and a full-off condition. To the contrary, such blinking can simply be a variation between a high state (e.g., bright light) and a low state (e.g., dim light), e.g., as illustrated in FIG. 4B.

In certain embodiments the frequency of blinking of the first light source (or spectral component thereof and/or the second light source (or spectral component thereof) ranges from about 20 Hz, or from about 30 Hz, or from about 35 Hz or from about 40 Hz up to about 100 Hz, or up to about 80 Hz, or up to about 60 Hz, or up to about 50 Hz, or up to about 45 Hz. In certain embodiments the frequency of blinking of the first light source (or spectral component thereof and/or the second light source (or spectral component thereof) ranges from about 20 Hz up to about 50 Hz. In certain embodiments the frequency of blinking of the first light source (or spectral component thereof and/or the second light source (or spectral component thereof) is about 40 Hz.

In certain embodiments the duration of the blinks of the first light source (or spectral component thereof) and/or the second light source (or spectral component thereof) ranges from about 1 ms, or from about 5 ms up to about 50 ms, or up to about 40 ms, or up to about 30 ms, or up to about 20 ms, or up to about 15 ms, or up to about 10 ms. In certain embodiments the duration of the blinks of the first light source (or spectral component thereof) and/or the second light source (or spectral component thereof) ranges from about 5 ms up to about 20 ms, or from about 8 ms up to about 15 ms.

In certain embodiments the color temperature of the first light source and/or second light source ranges from about 2700K, or from about 2800K, or from about 2900K up to about 6500K, or up to about 5000K, or up to about 4000K, or up to about 3500K. In certain embodiments the color temperature of the first light source and/or second light source ranges from about from about 2900K up to about 3100 K. In certain embodiments the color temperature of the first light source and/or second light source is about 3000K. As indicated above, in various embodiments, it is desirable to keep the difference in correlated color temperatures ΔT between the first light source and the second light source small (e.g., about 50K or less or about 30K, or about 20K or less, or about 10K or less, or about 5K or less, or in certain embodiments ranges from about 0.5K, or from about 1K or from about 5K up to about 10K).

In certain embodiments the first light source and/or the second light source provides a luminous intensity ranging from about 10 lm, or from about 25 lm, or from about 50 lm, or from about 100 lm, or from about 500 lm, up to about 10,000 lm, or up to about 5,000 lm, or up to about 1000 lm.

In certain embodiments the first light source provides irradiance that is larger than about 5 mW/nm/m$^2$ in a wavelength range from about 440 nm up to about 500 nm, or from about 450 nm up to about 490 nm, or from about 450 nm up to about 480 nm, or from about 450 nm up to about 470 nm, or from about 455 nm up to about 465 nm.

In certain embodiments the first light source light has a total illuminance and/or an illuminance of the blue spectral component of at least about 10 lux, or at least about 20 lux, or at least about 30 lux, or at least about 40 lux, or at least about 50 lux, or at least about 60 lux, or at least about 70 lux, or at least about 80 lux, or at least about 90 lux, or at least about 100 lux, or at least about 120 lux, or at least about 130 lux, or at least about 140 lux, or at least about 150 lux, or at least about 160 lux, or at least about 170 lux, or at least about 180 lux, or at least about 190 lux, or at least about 200 lux, or at least about 300 lux, or at least about 400 lux, or at least about 500 lux, or at least about 600 lux, or at least about 700 lux, or at least about 800 lux, or at least about 900 lux, or at least about 1000 lux.

In certain embodiments the second light source light has a total illuminance of at least about 10 lux, or at least about 20 lux, or at least about 30 lux, or at least about 40 lux, or at least about 50 lux, or at least about 60 lux, or at least about 70 lux, or at least about 80 lux, or at least about 90 lux, or at least about 100 lux, or at least about 120 lux, or at least about 130 lux, or at least about 140 lux, or at least about 150 lux, or at least about 160 lux, or at least about 170 lux, or at least about 180 lux, or at least about 190 lux, or at least about 200 lux, or at least about 300 lux, or at least about 400 lux, or at least about 500 lux, or at least about 600 lux, or at least about 700 lux, or at least about 800 lux, or at least about 900 lux, or at least about 1000 lux.

In certain embodiments the distance to the black body locus DUV for the first light source and the second light source is less than about 0.01, or less than about 0.001, or less than about 0.0001. In certain embodiments the distance to the blackbody locus DUV for the first light source and the second light source is about 0.0001 or less.

In certain embodiments the difference in intensity between the first light source and the second light source is less than about 100 lux, or less than about 75 lux, or less than about 50 lux, or less than about 40 lux, or less than about 30 lux, or less than about 20 lux, or less than about 10 lux, or less than about 5 lux, or less than about 2 lux.

Figure 10:
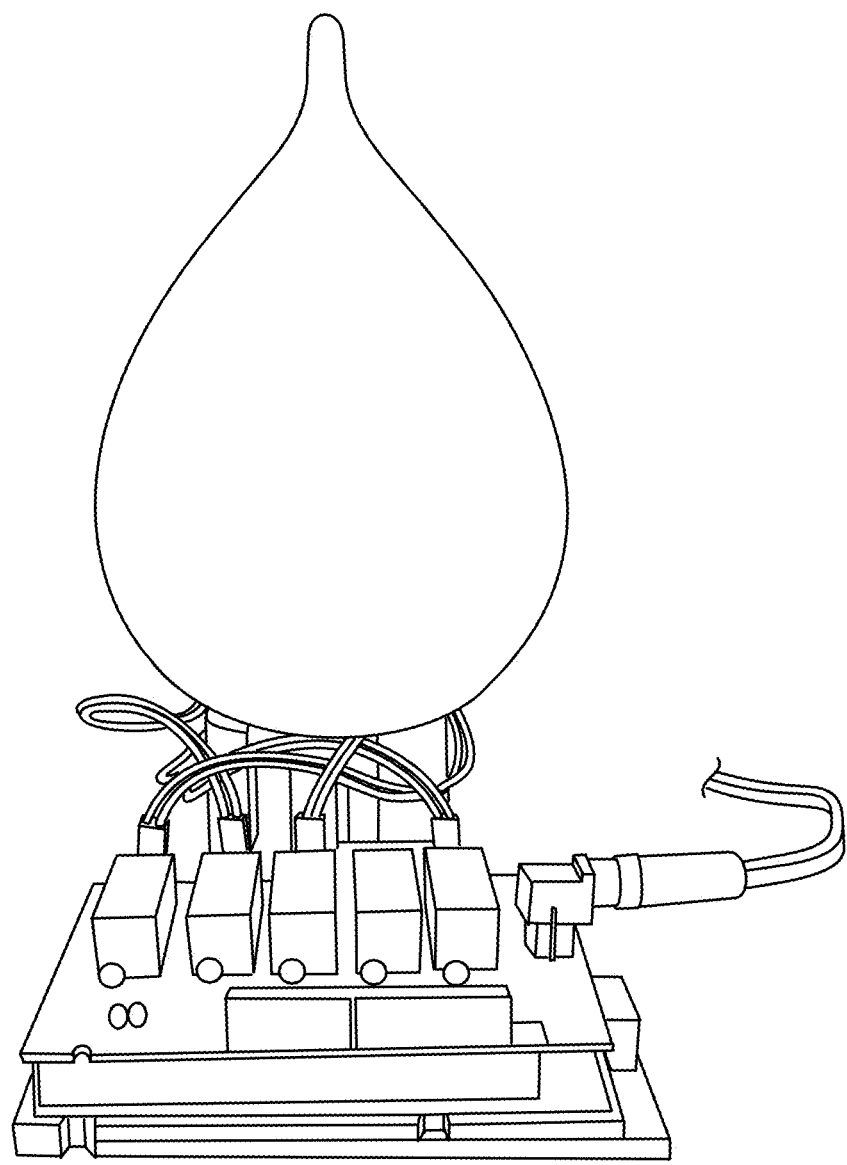
FIG. 10 shows an illustrative diffuser mounted on top of LEDs comprising a light source.

In various embodiments illustrative, but non-limiting embodiments, the first light source and the second light source emit light in substantially the same direction. In certain embodiments the difference in illumination angel between the first light source and the second light source is less than about 30 degrees, or less than about 25 degrees, or less than about 20 degrees, or less than about 15 degrees, or less than about 10 degrees, or less than about 5 degrees, or less than about 3 degrees, or less than about 1 degree. In certain embodiments the co-alignment of illumination direct is accomplished by providing the phototherapy device with a diffuser (see, e.g., 108 in FIG. 1, and image in FIG. 10) and/or a collimator.

In certain embodiments the light source comprises or consists of a blue spectral component, a green spectral component, and an orange or red spectral component. This can be accomplished, inter alia, by providing the first light source with a lamp that emits primarily a blue light, a lamp that emits primarily a green light, and a lamp that emits primarily an orange and/or red light. In certain embodiments the blue light comprising the first light source, or the blue spectral component of the first light source, or the blue light emitted by a lamp is in the wavelength range from about 440 nm up to about 495 nm, or from about 440 nm up to about 480 nm, or from about 450 nm up to about 480 nm, or from about 450 nm up to about 470 nm. In certain embodiments the blue light comprising the first light source, or the blue spectral component of the first light source, or the blue light emitted by a lamp has a maximum emission at about 460 nm.

In certain embodiments the green light comprising the first light source, or the green spectral component of the first light source, or the green light emitted by a lamp comprising the second light source is primarily in the wavelength range from about 495 nm up to about 570 nm, or from about 500 nm, or from about 510 nm, or from about 520 nm, or from about 530 nm, or from about 540 nm, or from about 550 nm up to about 570 nm. This can be accomplished, inter alia, by providing the first light source with a lamp that emits primarily in the wavelength range from about 550 nm up to about 570 nm. In certain embodiments the green light comprising the first light source, or the green spectral component of the first light source, or the green light emitted by a lamp has a maximum emission at about 550 nm or at about 570 nm.

In certain embodiments the orange/red light comprising the first light source, or the orange/red spectral component of the first light source, or the orange/red light emitted by a lamp comprising the second light source is primarily in the wavelength range from about 590 nm up to about 750 nm, or from about 600 nm up to about 700 nm, or up to about 650 nm. In certain embodiments the orange/red light comprising the first light source, or the orange/red spectral component of the first light source, or the orange/red light emitted by a lamp is primarily in the wavelength range from about 600 nm up to about 650 nm. In certain embodiments the orange/red light comprising the first light source, or the orange/red spectral component of the first light source, or the orange/red light emitted by a lamp has a maximum emission at about 600 nm or at about 650 nm.

In certain embodiments the second light source comprises or consists of a blue/green spectral component, an orange spectral component, and a red/far red spectral component; or the second light source comprises or consists of a green spectral component, and an orange/red spectral component. In certain embodiments the second light source comprises or consists of a lamp that emits primarily a blue/green light, a lamp that emits primarily an orange light, and a lamp that emits primarily a red/far red light; or the second light source comprises or consists of a lamp that emits primarily a green light, and a lamp that emits primarily an orange/red light.

In certain embodiments the second light source comprises or consists of a lamp that emits primarily a blue/green light, a lamp that emits primarily an orange light, and a lamp that emits primarily a red/far red light.

In certain embodiments the blue/green light comprising the second light source, or the blue/green spectral component of the second light source, or the blue/green light emitted by a lamp comprising the second light source is primarily in the wavelength range from about 490 nm up to about 570 nm, or from about 500 nm, or from about 510 nm, or from about 520 nm, or from about 530 nm, or from about 540 nm, or from about 550 nm up to about 570 nm. In certain embodiments the blue light comprising the second light source, or the blue spectral component of the second light source, or the blue light emitted by a lamp has a maximum emission at about 490 nm.

In certain embodiments the orange light comprising the second light source, or the orange spectral component of the second light source, or the orange light emitted by a lamp comprising the second light source is primarily in the wavelength range from about 590 nm up to about 620 nm, or from about 590 nm up to about 610 nm. In certain embodiments the orange light comprising the second light source, or the orange spectral component of the second light source, or the orange light emitted by a lamp comprising the second light source has a maximum emission about 600 nm.

In certain embodiments the red/far red light comprising the second light source, or the red/far red spectral component of the second light source, or the red/far red light emitted by a lamp comprising the second light source is primarily in the wavelength range from about 620 nm, up to about 770 nm, or from about 650 nm up to about 750 nm, or from about 670 nm up to about 700 nm. In certain embodiments the the red/far red light comprising the second light source, or the red/far red spectral component of the second light source, or the red/far red light emitted by a lamp comprising the second light source is primarily is 670 nm or about 770 nm.

In certain embodiments the second light source comprises or consists of a lamp that emits primarily a green light, and a lamp that emits primarily an orange/red light. In certain embodiments the green light comprising the light emitted by the second light source, or the green spectral component of the second light source, or the green light emitted by a lamp comprising the second light source is primarily in the wavelength range from about 495 nm up to about 570 nm, or from about 500 nm, or from about 510 nm, or from about 520 nm, or from about 530 nm, or from about 540 nm, or from about 550 nm up to about 570 nm. In certain embodiments the second light source, or the green spectral component of the second light source, or the green light emitted by a lamp is primarily in the wavelength range from about 500nm up to about 550 nm. In certain embodiments the green light comprising the second light source, or the green spectral component of the second light source, or the green light emitted by a lamp has a maximum emission at about 500 nm. In certain embodiments the orange/red light comprising the second light source, or the orange/red spectral component of the second light source, or the orange/red light emitted by a lamp comprising the second light source is primarily in the wavelength range from about 590 nm up to about 750 nm, or from about 600 nm up to about 700 nm, or up to about 650 nm. In certain embodiments the orange/red light comprising the second light source, or the orange/red spectral component of the second light source, or the orange/red light emitted by a lamp is primarily in the wavelength range from about 600 nm up to about 650 nm. In certain embodiments the orange/red light comprising the second light source, or the orange/red spectral component of the second light source, or the orange/red light emitted by a lamp has a maximum emission at about 600 nm or at about 610 nm.

Figure 11:
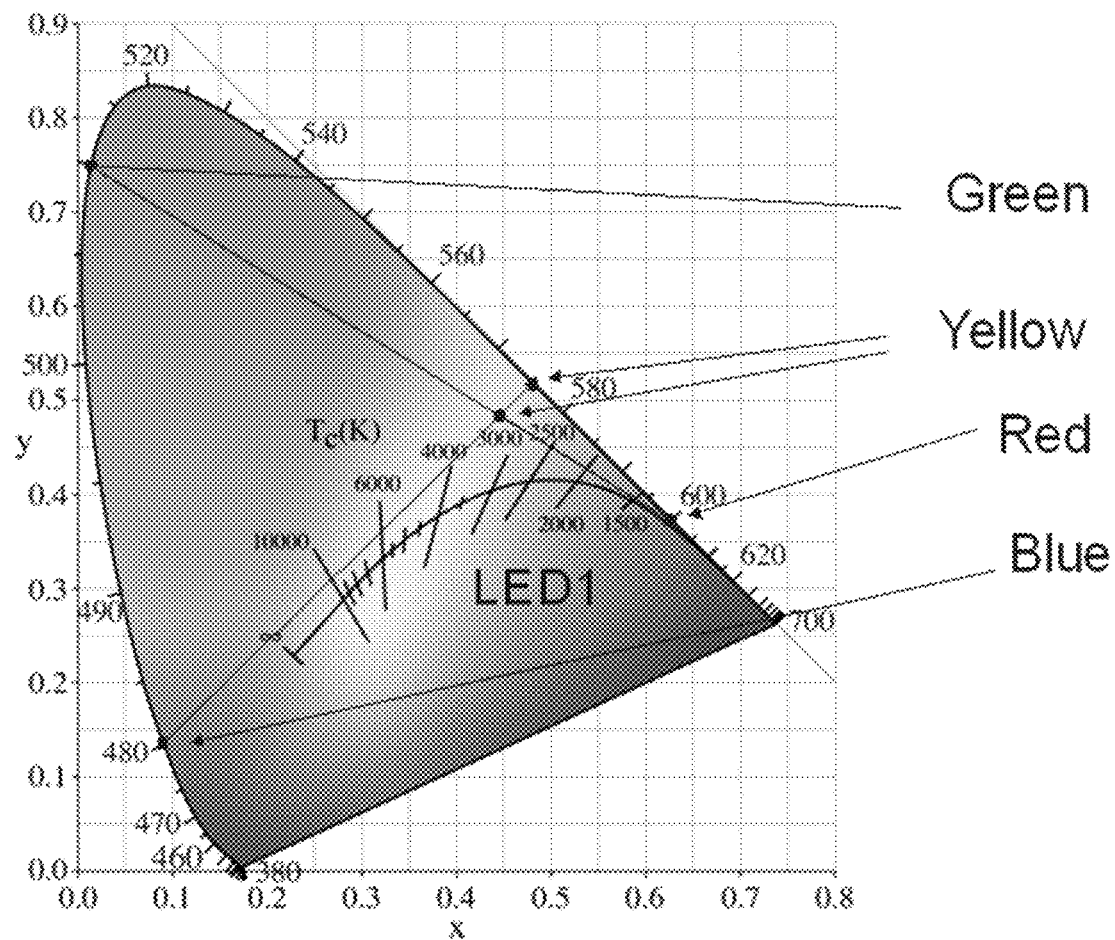
FIG. 11 shows an illustrative, but non-limiting chromaticity diagram for the generation of a colored (e.g., yellow) light in a phototherapy device.

In certain embodiments the phototherapy devices described herein can be operated in a colored mode. A specific color can be generated by the mixing of different colors. For example, it is possible to generate a yellow color by the mixing of red light, e.g., at 630 nm and green light at 530 nm (see, e.g., FIG. 11). The visual cortex in the brain will combine the red color and the green color into a yellow color that will have the same visual appearance for humans as a pure yellow color at 580 nm (which is just in the middle of the interval from 530 nm to 630 nm). Thus, for example, it is possible to provide a yellow therapeutic lamp that oscillates between a first light source comprising a spectral component at about 630 nm (red) and a spectral component at about 530 nm (green), and a second light source comprising a spectral component at about 580 nm (yellow). Note that while hippocampal stimulation is readily accomplished using a blue light, it is believed that hippocampal stimulation can also be accomplished using a flashing green light (or a combination of flashing blue and/or green lights). When the first light source and second light source are flashed out of phase, the blinking of the light at, for example, 40 Hz, will not be perceptible, however, it will modulate the brain since 530 nm give a larger modulation in the hippo campus than 580 nm light. This principle may extended even further to incorporate blue light at, for example, about 470nm to about 480 nm, a wavelength range that is very effective for brain modulation relevant for treatment of Alzheimer's. Thus, for example, in the chromaticity diagram shown in FIG. 11 it is shown how the same yellow color made can be made using a first light source comprising of blue at about 480 nm and yellow at about 575nm with a second light source providing color mixing of green at about 510 nm and red at about 600 nm. These combinations are illustrative and non-limiting. Using the teaching provided herein a phototherapy device comprising first light source (proving a blue and/or a green blinking component) and a second "complementary" light source that when combined with the light from said first light source provides illumination in which the blinking is substantially undetectable by human vision will be readily available to one of skill and capable of offering illumination in a variety of colors.

In certain embodiments the phototherapy device may comprise one or more optical elements, such as a diffuser, lenses, lens arrays, micro-lenses, micro-lens arrays, reflectors, diffractive optical elements, etc., positioned in respective propagation paths of light emitted by the first and/or second light sources for directing the emitted light into desired directions.

Control Mechanism

In certain embodiments the light therapy devices described herein can comprises a control mechanism (a controller, see, e.g., 110 in FIG. 1) that controls the emission spectrum from the first light source and/or the second light source (e.g., a narrow and/or a broad spectrum light source). In certain embodiments the phototherapy device in combination with a controller and/or in combination with, e.g., a personal information device as described below, may comprise a light therapy (phototherapy) system.

In certain embodiments the controller may simply provide an on-off and/or brightness control (see, e.g., 112 in the illustrative, but non-limiting embodiments shown in FIG. 1). However, in certain embodiments numerous other functions may be controlled. In certain embodiments illustrative controls can include one or more of the following: on/off and/or brightness (112 FIG. 1), a blink frequency control (113 FIG. 1), a phase and/or duty cycle control ((114 FIG. 1), a color temperature and/or hue control (115 FIG. 1), and the like.

In certain embodiments the blinking blue light component (e.g., a narrow spectrum light source and/or first light source) emits for a shorter time period than the broad spectrum light source. In such embodiments, the brain is stimulated at certain times of the day or night to induce oscillations (e.g., gamma oscillations). As this may alter circadian rhythms of a person, it can be desirable to stimulate the brain only at certain times of day, while providing constant illumination (without an oscillating component) at other times of the day or night.

The controller may also adjust the brightness and/or color temperature of the phototherapy device in response to changes in ambient lighting conditions. Thus, for example during daylight hours the phototherapy device may operate at higher intensities (brightens) than during nighttime hours.

Figure 8:
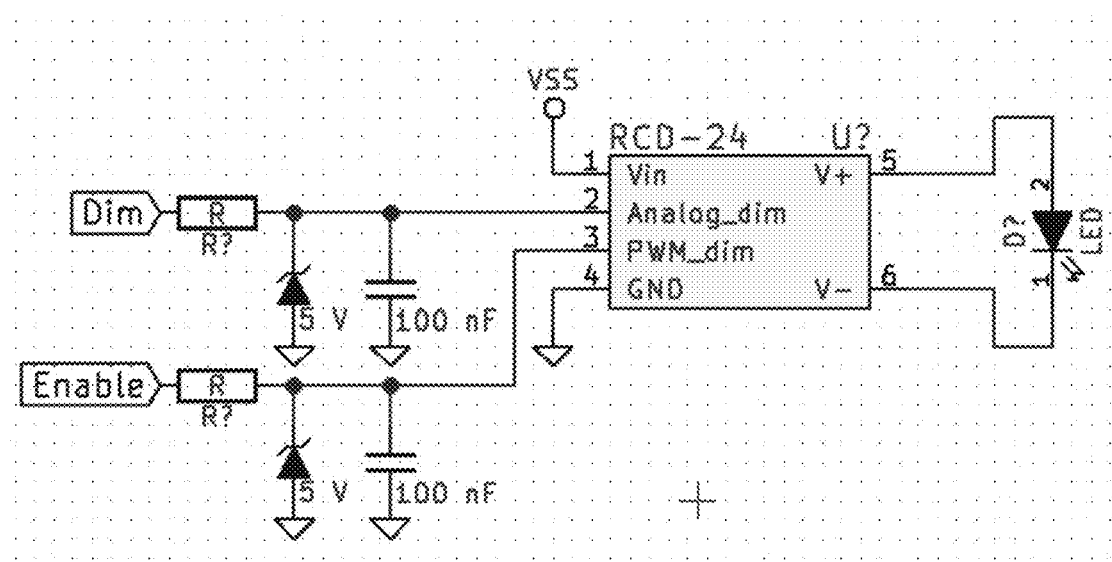
FIG. 8 shows one illustrative, but non-limiting embodiment of a circuit that can drive a light source comprising a phototherapy device described herein.
Figure 9:
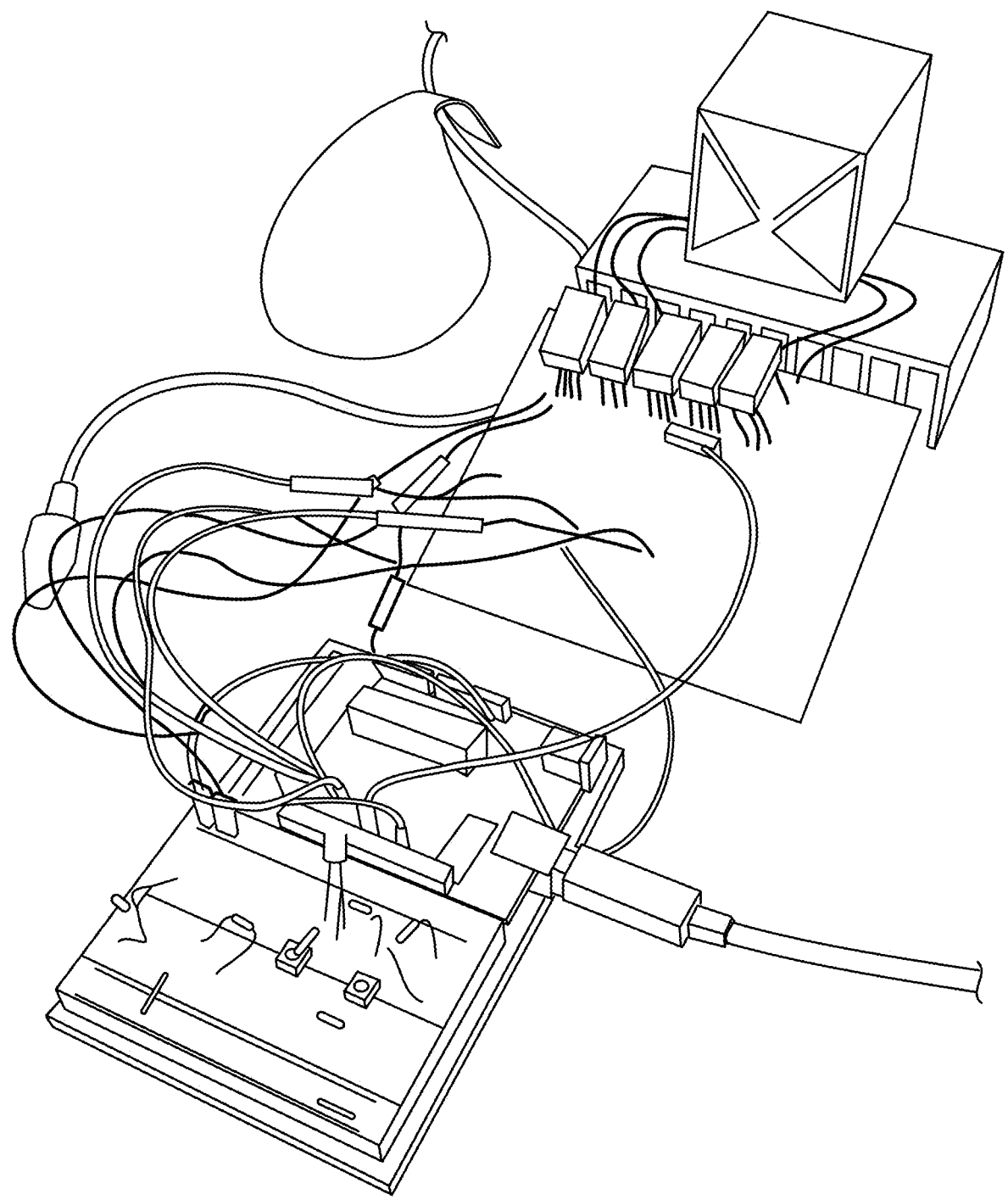
FIG. 9 shows a prototype of one embodiment of a phototherapy device described herein.
Figure 12:
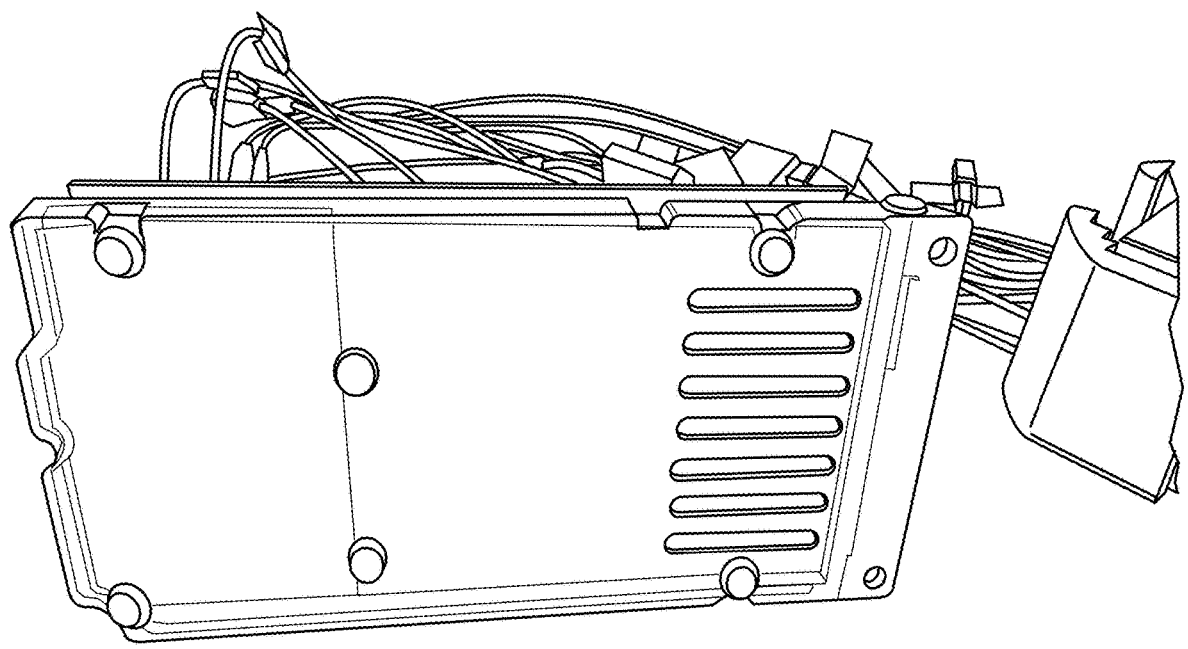
FIG. 12 illustrates an Arduino micro-controller useful in the phototherapy devices described herein.
Figure 13:
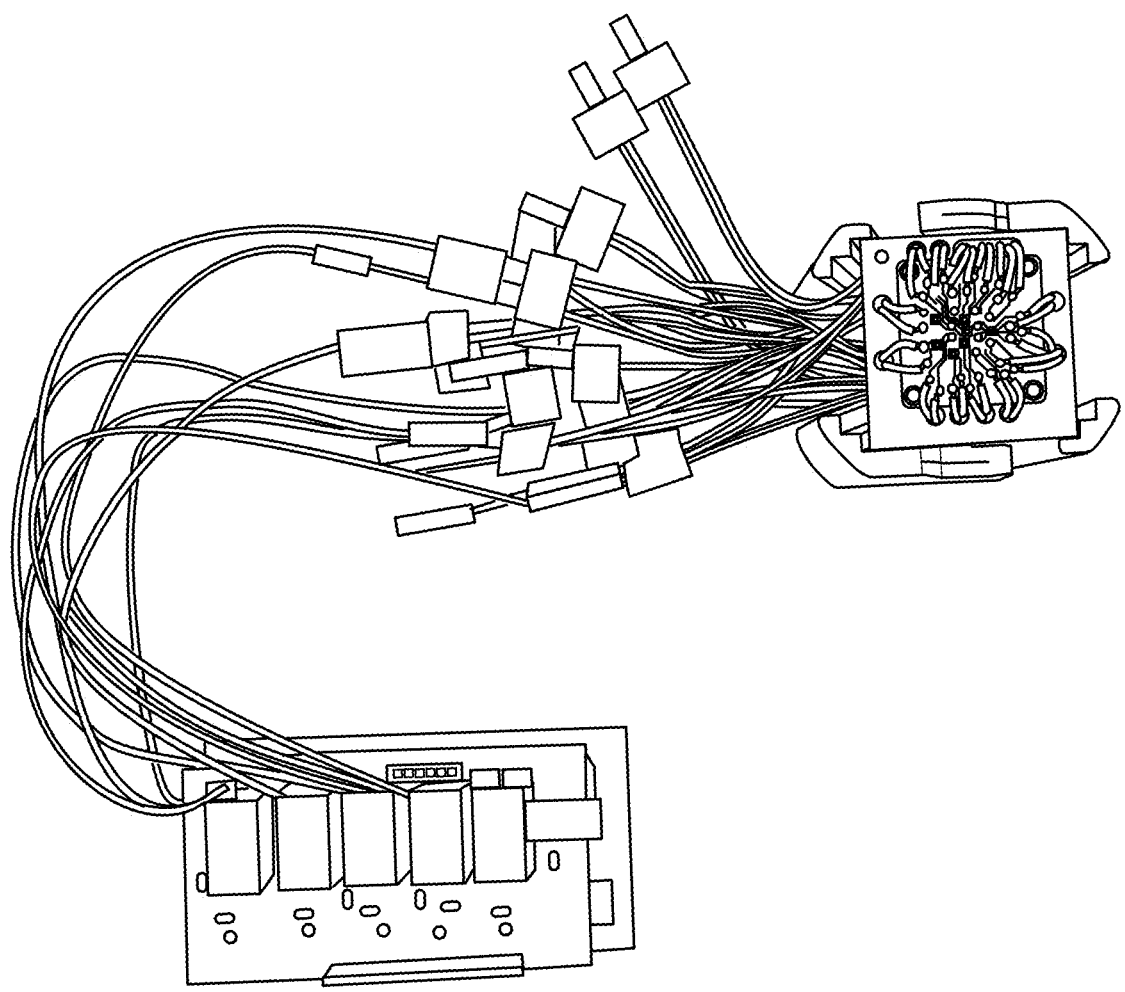
FIG. 13 illustrates LEDs with mounts, driver electronics and micro-controller all wired up.
Figure 14:
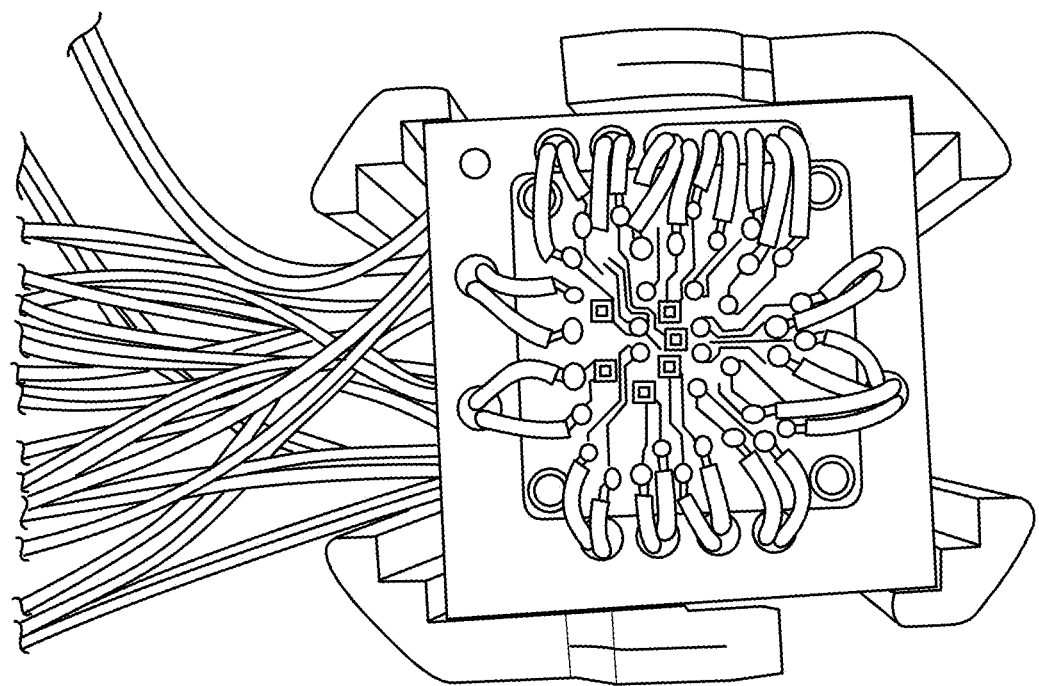
FIG. 14 shows a close-up of LEDs in one embodiment of the devices described herein.

One illustrative, but non-limiting embodiment of control circuitry for operating a light source comprising the phototherapy device described herein is shown in FIG. 8 shows one illustrative, but non-limiting embodiment of a circuit that can drive a light source comprising a phototherapy device described herein. In one illustrative, but non-limiting embodiment the phototherapy device comprises five LEDs that form two different light sources (see, e.g., FIG. 1). In certain embodiments the driver electronics can be identical for each LED. A micro-controller can provide signals to the "Dim" and "Enable" ports to enable the desired flickering and phase difference (e.g., 180 degree phase difference) between the two light sources. As an example of the microcontroller, in certain embodiments an Arduino MEGA2560 micro-controller (see, e.g., FIG. 12) to generate the timing signals for the LEDs, but other micro-controllers or computers can be used. FIG. 13 illustrates the LEDs with mounts, driver electronics and micro-controller all wired up. FIG. 14, provides a close-up view of the LEDs. It will be recognized that these embodiments are illustrative and non-limiting. Using the teaching s provided herein, numerous variations of controllers, control circuitry, light sources, and lamps will be available to one of skill in the art.

In this regard, it is noted that in certain embodiments the controller is integral to the device (e.g., incorporated into the housing of the device), while in other embodiments, the controller may be remote from the device and coupled by a control cable or cables ((see, e.g., 109 in the illustrative, but non-limiting embodiments shown in FIG. 1). In other embodiments the controller may control the phototherapy device through a radio link, a light (e.g., infra-red link), via a Bluetooth link, and via a WiFi link. In certain embodiments the controller comprises an App on a cell phone, tablet, or computer. Thus, in certain embodiment, the controller may be accommodated in a housing separate from the phototherapy device housing. For example, the controller may reside in a separate room of a building comprising a plurality of rooms, each of which contains a phototherapy device controlled by the controller, e.g. in response to ambient light intensity, e.g., as sensed by one or more light sensors as described above and/or possibly, or in response to the time of day.

In certain embodiments the controller may be interconnected with one or more phototherapy devices cables containing signal lines (see, e.g., 109 in FIG. 1) for provision of control signals from the controller to the phototherapy device.

In certain embodiments the controller may be wirelessly interconnected with one or phototherapy device(s) for wireless transmission of control signals from the controller to the respective device(s). For example, the light controller and a phototherapy device may comprise an interface to a wired Local Area-Network (LAN) and/or to a wireless LAN (BlueTooth, WiFi), and/or a to a mobile telephone network, and/or to another Wide-Area-Network (WAN), such as the internet. In this way networks already present may be utilized for control of the phototherapy device.

Further, utilizing a LAN or a WAN, such as the Internet, makes it possible for time keeping units and light sensors and other sensors and user interfaces and the controller and other parts of the phototherapy device/system to reside in separate locations possibly separated by large distances. For example, the controller software may reside on a server, or may be distributed among a plurality of servers, connected to the Internet and thus residing anywhere in the world in a location with Internet access.

In certain embodiments the phototherapy device/system may comprise a hand-held unit that is configured for connection to the phototherapy device and has a user interface configured for user entry of user data, and where the hand-held unit is configured to transmit the user data to the controller, and where the light controller is configured for controlling the phototherapy device in response to the user data.

In certain embodiments the hand-held unit may be a desktop computer, a laptop computer, a smartphone, a tablet, a wearable computer, such as a smartwatch, an activity tracker, etc., and may have an interface to a Wired Local-Area Network (LAN) and/or a wireless LAN (BlueTooth, WiFi), and/or a mobile telephone network, and/or a Wide-Area-Network (WAN), such as the internet, and may be configured to be interconnected with a remote server through the network, e.g. for storage of data from sensors of the hand-held unit, for entry of user data, etc.

Through the Wide-Area-Network, e.g. the Internet, the controller may have access to data, such as personal health data and/or electronic time management and/or data provided by communication tools relating to and used by one or more users of the phototherapy device. In certain embodiments the tools and the stored information typically reside on one or more remote servers accessed through the Wide-Area-Network. In certain embodiments a plurality of devices, e.g. user's smartphones, with interfaces to the Wide-Area Network may access the one or more remote servers through the Wide-Area-Network and may be used to enter information relating to the users.

The tools may Include electronic calendar system(s), email system(s), such as Microsoft Outlook, Windows Mail, Mozilla Thunderbird, Apple Mail, Opera Mail, Hotmail, Gmail, etc., social network(s), professional network(s), such as Facebook®, LinkedIn®, Google+, Twitter, etc., well-known for management of appointments and other daily activities and communications. Other tools include, but are not limited to web-based health management systems hosted by a health care provider (e.g., an insurance company, an HMO, etc.), or commercial internet health management services (e.g., Nokia/Withings, Internet Health Mgmt (®HealthMgmt), etc.).

In certain embodiments the controller, or a part of the controller, may reside on a hand-held unit. A user interface for the phototherapy device may reside on a smartphone, and the smartphone may execute an app allowing the user to control the phototherapy device, e.g. for adjustment of one or more parameters, e.g., as described above.

In certain embodiments control (controller) software comprises means to take into account the individual's personal data, and preferably quantified-self data from individual sensor(s) and/or tracker(s). In certain embodiments the control software comprises means to take into account the athlete's travel, training and competition program in order to optimize training and/or performance at race events. In certain embodiments the control software runs semi- or fully-automatic with little or no interaction from the individual/user. In other embodiments, data collection of various parameters relevant for the individual is gathered using one or more sensors, for example in the form of a wearable sensor.

In certain embodiments the system comprises an app-based interface, a cloud-based database and means for analyzing individual data. In a further preferred embodiment, the system comprises means for providing personal training advice/guidance. In certain embodiments the systems and devices described herein are used by an athlete during training periods and/or for competitions. It is an advantage that the systems and devices described herein enable the athlete to optimize sleep during intense training and/or competition programs. This is important as sleep is a critical parameter for recovery, and an athlete's reaction speed and ability to perform at maximum level.

Further, in certain embodiments the system uses an additional light source with stroboscopic effect to illuminate a human from above on his/her head, whereby brain activity is increased.

Phototherapy Device Configurations

In certain embodiments the phototherapy devices described herein can adopt any of a number of configurations. Thus, for example, in certain embodiments, the phototherapy devices described herein comprises a lamp or a luminaire, such as a lamp or luminaire positioned in a room, from a ceiling, a stationary (standing) lamp, a desk lamp, a wall mounted lamp (e.g., a reading lamp), etc.).

In certain embodiments the phototherapy devices described herein operate over an extended time during a person's sleep. In certain embodiments the extended time is 1/2 hour or more, or about one hour or more, or about 1.5 hours or more, or about 2 hours or more (for example continuously over 1/2 hour or more, or about one hour or more, or about 1.5 hours or more, or about 2 hours or more, or in multiple time segments that total 1/2 hour or more, or about one hour or more, or about 1.5 hours or more, or about 2 hours or more per night). In certain embodiments the phototherapy device comprises a sleep mask that provides a blinking blue spectral component, e.g., as described above. The present inventors have further realized a method where a person is using such a system, wherein the blinking blue light source illuminates a person's eyelids during sleep. The system enables retinal ganglion cells to be exposed be a fraction of the emitted stroboglopic blue light in a sufficient time and intensity to positively affect or stimulate desired parts of the brain.

In certain embodiments the phototherapy device(s) or the first and/or second light sources comprising the phototherapy devices described herein may be configured for mounting proximate, or at, and/or attached to, a frame of a window, for example attached to the frame of the window, the window being mounted in a wall of a room for daylight illumination of the room through the window pane.

In certain embodiments the proximity of the phototherapy devices or the first and/or second light sources comprising the phototherapy devices fitting to the window, preferably the distance is less than 50 cm, preferred less than 25 cm, more preferred less than 10 cm, most preferred less than 5 cm, which causes the light emitted by the phototherapy device to be perceived as a part of the natural daylight illuminating the room through the window pane. In particular for elderly or individuals in mentally challenged circumstances, the perception of alienating or intruding technology may have a negative or sub-optimum effect.

In certain embodiments the phototherapy device(s) or the first and/or second light sources comprising the phototherapy devices described herein may be mounted so that the frame of the window is illuminated by the phototherapy device(s) or the first and/or second light sources comprising the phototherapy devices described herein and the room is illuminated by light from the phototherapy device(s) or the first and/or second light sources comprising the phototherapy devices described herein that has been reflected, e.g. diffusely reflected, into the room by the frame of the window.

For example, the phototherapy device(s) or the first and/or second light sources comprising the phototherapy devices described herein be mounted so that the light emitted by the light source is directed towards a part of the frame when the phototherapy device is mounted in its intended position for use, whereby light emitted by the phototherapy device is reflected by the frame of the window for illumination of the room in combination with sunlight entering the room through the Window pane. The illuminated parts of the frame may be coated with a reflective material for improved illumination of the room.

In this manner a room may unobtrusively be administered a prophylactic or therapeutic light regimen as described herein.

In certain embodiments the phototherapy devices comprise a hardware part having one or more LED-based luminaires. Optionally, the system also includes ceiling and/or table top luminaires. In certain embodiments the system may comprise head-mounted luminaires, for example light sources integrated into sleep masks and/or glasses.

In certain embodiments the system is configured for use by individual (for example a patient, a prisoner, a student, an elderly individual in a private home, or an athlete) for optimizing rehabilitation, recovery, physiotherapy, practice, training and/or performance at competition.

In certain embodiments the phototherapy devices described herein are adapted to emit stroboscopic (blinking) light during morning hours, such as from 6 am to 11 am, or a shorter time period within the morning hours. In certain embodiments the blue light source is emitting light at a predetermined time period defined by a user and/or defined by an algorithm. In certain embodiments the predefined algorithm may be designed to stabilize a human's circadian rhythm. The algorithm may be based on machine-learning to tailored the stabilization via data collected from a tracking device and/or personalized human data from e.g. DNA sequencing.

It is within the scope of the invention to combine a light therapy system with non-invasive monitoring of activity, temperature, light exposure, and other parameters, e.g., as described below. It is further within the scope to combine such embodiments with measurement of salivary hormone concentrations, and/or markers of amyloidogenic pathologies, and/or cognitive and behavioral functioning, in order to analyze the consequences of the light exposure on circadian and mental health.

Also within the scope of the present invention is the combination of stroboscopic light (blinking light) as described herein with sound waves. Examples of sound waves and light combinations for increased brain activity are described by Vandewalle et al. (2010) *Proc. Natl. Acad. Sci. USA*, 107: 19549-19554. A person skilled in the art of sound systems would be able to combine sound waves into a system of the present invention.

In other preferred embodiments, a system according to the invention is used during treatment of cataracts. Such treatment can give more light from 440 nm to 540 nm at the non-visual ganglion cells at the retina and therefore increased brain activity via the stroboscopic light.

Personal Information/Tracking

In certain embodiments the phototherapy devices and/or controllers described herein are configured with a personal information device into a phototherapy system. Accordingly, in some embodiments, the system further comprises a personal tracking device that records parameters including a person's body temperature, activity, movement, heart rate, blood pressure, and/or exposure to UV light.

Accordingly, in certain embodiments, the phototherapy system may comprise one or more personal environment sensors configured to be worn by a human, e.g. selected from the group consisting of accelerometer, gyroscope, compass, ambient light sensor, UV sensor, GPS-unit, and barometer, and wherein the phototherapy device controller is configured for controlling the phototherapy device in response to parameter values output by one or more personal environment sensors.

In certain embodiments the phototherapy device may, for example, be interconnected with wearables used by a human, such as smart phones, smart watches, such as the Apple Watch, the Samsung Gear, the Pebble Watch, etc., activity trackers, such as the Fitbit Flex and others by Fitbit, the Garmin Vivofit or others by Garmin, the Sony Smartband or others by Sony, etc., etc., utilizing data from their sensors, typically including an ambient light sensor, GPS, an accelerometer, a clock, etc.

In certain embodiments the measured/recorded parameters are used to analyze a person circadian rhythm and track their activity throughout the day using machine learning to personally optimize an individual's circadian rhythm and/or to optimize the subject's cognitive performance. In certain embodiments the personal tracking device will further be able to transmit information to a centralize cloud system that can then be utilized to detect any disruption in circadian rhythms and/or cognitive performance. In certain embodiments the cloud system can also be utilized to communicate with personal devices and automatically control lighting systems as a tool for personalized medicine.

In certain embodiments the tracking device uses a wireless connection, such as a blue tooth and or WIFI connection.

In certain embodiments the phototherapy device and/or controller has an interface to a network and is configured to be interconnected with a remote server through the network for performing at least one of the operations selected from the group consisting of utilizing computing resources of the remote server to control the light source, access personal data relating to a human using the system, and access data relating to the environment of the system.

In various preferred embodiments, the system is used for health care and/or improvements in life quality of elderly people; for improvements in the performance of athletes (professionals as well as amateurs in a broad sense); for health care and/or improvements in life quality of people spending the majority of their awake time indoors, such as imprisoned people; for improvements in sleeping pattern of children, as well as for a number of other groups of people.

Multiple Devices and Combination Therapies

In certain embodiments the use of multiple phototherapy devices described herein is contemplated. For example, it is possible to use multiple devices (such as in a private home, an office, at a hospital room, etc.), and the individual devices can be synchronized (in such a manner that the blinking of the first and second light sources are controlled to be substantially at the same timings). One advantage of this is that the multiple devices can act as an illumination system (for example for general lighting) and at the same time, a person can be treated and/or exposed to light from multiple devices (without risking that the multiple devices cancel out each other, partly or fully). Another advantage is that multiple devices can be used to treat/expose a person, and for example make it easier to treat an AD patient who is struggling to be in one place for some time, or who is struggling to have handle a device, or who is not able to operate a device. Hence, in certain embodiments, an automated system with multiple devices that ensure that the person receives the light therapy irrespective of how the person is moving around, is contemplated.

Additionally, it is recognized that the phototherapy devices described herein can be used in combination with other methods of neural stimulation and/or with various pharmaceuticals (e.g., pharmaceuticals for use in the treatment of dementia and/or Alzheimer's disease). Thus, for example, in certain embodiments, the phototherapy devices and/or systems described herein are used in combination with other means for neural stimulation, such as sound, physical vibration, electrical, transcranial magnetic stimulation, and the like.

In certain embodiments the phototherapy devices described herein are used in combination with treatment using various neuropharmaceuticals. Such neuropharmaceuticals include, but are not limited to, cholinesterase inhibitors such as donepezil (ARICEPT®), galantamine (RAZADYNE®), rivastigmine (EXELON®), and the like. Other neuropharmaceuticals include, but are not limited to antipsychotic medications for hallucinations, delusions, aggression, agitation, hostility, and/or uncooperativeness. Such medications include, but are not limited to, aripiprazole (ABILIFY®), clozapine (CLOZARIL®), haloperidol (HALDOL®), olanzapine (ZYPREXA®), quetiapine (SEROQUEL®), risperidone (RISPERDAL®), ziprasidone (GEODON®), and the like.

Uses of Phototherapy Devices and Systems

The phototherapy devices and systems described herein can be for health care and/or improvements in life quality of elderly people, for improvements in the performance of athletes (professionals as well as amateurs in a broad sense), for health care and/or improvements in life quality of people spending the majority of their awake time indoors, such as imprisoned people; for improvements in sleeping pattern of children, as well as for a number of other groups of people. The phototherapy devices and systems described herein provide a lighting system for improved health care and/or life quality of an individual and can be used for optimization of an individual's performance in a mentally and/or physically demanding situation, such as a meeting, a performance, a sports activity, a competition etc.

In various embodiments the phototherapy devices described herein are believed to be useful for the prophylaxis or treatment of neurodegenerative disorders including, but not limited to Alzheimer's disease, mild cognitive impairment (MCI), depression, dementia, short-term memory, or for improved learning, improved athletic performance or improved cognitive performance.

Increasing life expectancy, combined with the deterioration of biological processes with advancing age, necessitates the development of technologies that promote healthy aging. One often overlooked variable that contributes markedly to age-related cognitive and somatic disease is the degradation of rhythmic biological functioning. Precise rhythmic patterns of neural activity and physiological functioning are required for optimal health and disease prevention. With advancing age, circadian (daily) rhythms degrade and the ability of the brain circadian clock to synchronize to local time diminishes.

Consequently, aged individuals experience a loss of temporal coordination among central and peripheral systems, accelerating the aging process and contributing to age-related disease and cognitive decline. Specialized retinal ganglion cells sensitive to blue light communicate directly to the brain's master circadian clock, making these cells ideal targets to ameliorate age-related circadian decline. In addition, recent findings indicate an appropriate frequency of light (e.g., 40 Hz) can reverse the neural damage resulting from Alzheimer's disease in a mouse model (see, e.g., Iaccarino et al. (2016) Nature, 540(8): 230-252).

Uses of the phototherapy devices and/or systems described herein includes elderly care with patients suffering from Alzheimer's disease. The phototherapy devices and/or systems described herein may be implemented in elderly homes. The present invention will provide additional advantages to the health care industry and address Alzheimer's patients specifically.

In certain embodiments other embodiments, the phototherapy devices and/or systems described herein are used during treatment of cataracts.

Uses of the phototherapy devices and/or systems described herein includes the sports and athlete domain. For example, a sport team may use the phototherapy devices and/or systems described herein in a manner where the team acquires a set of phototherapy systems (one for each individual athlete on the team). The invention includes a service to control the lighting for optimized lighting for the individual athletes. The invention further enables teams to quantify and predict potential neural desynchronisis (such as from jetlag) and optimize recovery and sleep with respect to performance.

Professional sport teams suffer degraded performance due to disturbed circadian rhythm and the present invention provides technologies and a service to optimize sleep and recovery for the athletes. The phototherapy devices and/or systems described herein further enable prediction of potentially long-term, harmful head injuries (such as mild or severe concussion) and aid the athlete in optimal recovery. Hence, the phototherapy devices and/or systems described herein can be used by athletes, such as swimmers, badminton, basketball, baseball, soccer players, etc.

Therapeutic and Prophylactic Methods

In various embodiments therapeutic and/or prophylactic methods are provided that utilize the phototherapy devices and/or systems described herein. Typically, the methods involve exposing a subject to a light regimen described herein for a duration and intensity sufficient to induce or entrain oscillatory brain activity (e.g., gamma oscillations) that have been shown to decrease AP.

Prophylaxis

In certain embodiments he phototherapy devices and/or systems described herein are utilized in various prophylactic contexts. Thus, for example, in certain embodiments, the he phototherapy devices and/or systems described herein can be used to prevent or delay the onset of a pre-Alzheimer's cognitive dysfunction, and/or to ameliorate one more symptoms of a pre-Alzheimer's condition and/or cognitive dysfunction, and/or to prevent or delay the progression of a pre-Alzheimer's condition and/or cognitive dysfunction to Alzheimer's disease.

Accordingly in certain embodiments, the prophylactic methods described herein are contemplated for subjects identified as "at risk" and/or as having evidence of early Alzheimer's Disease (AD) pathological changes, but who do not meet clinical criteria for MCI or dementia. Without being bound to a particular theory, it is believed that even this "preclinical" stage of the disease represents a continuum from completely asymptomatic individuals with biomarker evidence suggestive of AD-pathophysiological process(es) (abbreviated as AD-P, see, e.g., Sperling et al. (2011) Alzheimer's & Dementia, 1-13) at risk for progression to AD dementia to biomarker-positive individuals who are already demonstrating very subtle decline but not yet meeting standardized criteria for MCI (see, e.g., Albert et al. (2011) Alzheimer's and Dementia, 1-10 (doi:10.1016/j.jalz.2011.03.008).

This latter group of individuals might be classified as "not normal, not MCI" but would be can be designated "pre-symptomatic" or "pre-clinical or "asymptomatic" or "pre-manifest"). In various embodiments this continuum of pre-symptomatic AD can also encompass, but is not necessarily limited to, (1) individuals who carry one or more apolipoprotein E (APOE) ε4 alleles who are known or believed to have an increased risk of developing AD dementia, at the point they are AD-P biomarker-positive, and (2) carriers of autosomal dominant mutations, who are in the presymptomatic biomarker-positive stage of their illness, and who will almost certainly manifest clinical symptoms and progress to dementia.

A biomarker model has been proposed in which the most widely validated biomarkers of AD-P become abnormal and likewise reach a ceiling in an ordered manner (see, e.g., Jack et al. (2010) Lancet Neurol., 9: 119-128.). This biomarker model parallels proposed pathophysiological sequence of (pre-AD/AD), and is relevant to tracking the preclinical (asymptomatic) stages of AD (see, e.g., FIG. 3 in Sperling et al. (2011) Alzheimer's & Dementia, 1-13). Biomarkers of brain amyloidosis include, but are not limited to reductions in CSF $A\beta_{42}$ and increased amyloid tracer retention on positron emission tomography (PET) imaging. Elevated CSF tau is not specific to AD and is thought to be a biomarker of neuronal injury. Decreased fluorodeoxyglucose 18F (FDG) uptake on PET with a temporoparietal pattern of hypometabolism is a biomarker of AD-related synaptic dysfunction. Brain atrophy on structural magnetic resonance imaging (MRI) in a characteristic pattern involving the medial temporal lobes, paralimbic and temporoparietal cortices is a biomarker of AD-related neurodegeneration. Other markers include, but are not limited to volumetric MRI, FDG-PET, or plasma biomarkers (see, e.g., Vemuri et al. (2009) Neurology, 73: 294-301; Yaffe et al. (2011) JAMA 305: 261-266).

In certain embodiments the subjects suitable for the prophylactic methods contemplated herein include, but are not limited to, subjects characterized as having asymptomatic cerebral amyloidosis. In various embodiments these individuals have biomarker evidence of Aβ accumulation with elevated tracer retention on PET amyloid imaging and/or low Aβ42 in CSF assay, but typically no detectable evidence of additional brain alterations suggestive of neurodegeneration or subtle cognitive and/or behavioral symptomatology.

It is noted that currently available CSF and PET imaging biomarkers of AP primarily provide evidence of amyloid accumulation and deposition of fibrillar forms of amyloid. Data suggest that soluble or oligomeric forms of AP are likely in equilibrium with plaques, which may serve as reservoirs. In certain embodiments it is contemplated that there is an identifiable preplaque stage in which only soluble forms of AP are present. In certain embodiments it is contemplated that oligomeric forms of amyloid may be critical in the pathological cascade, and provide useful markers. In addition, early synaptic changes may be present before evidence of amyloid accumulation.

In certain embodiments the subjects suitable for the prophylactic methods contemplated herein include, but are not limited to, subjects characterized as amyloid positive with evidence of synaptic dysfunction and/or early neurodegeneration. In various embodiments these subjects have evidence of amyloid positivity and presence of one or more markers of "downstream" AD-P-related neuronal injury. Illustrative, but non-limiting markers of neuronal injury include, but are not limited to (1) elevated CSF tau or phospho-tau, (2) hypometabolism in an AD-like pattern (i.e., posterior cingulate, precuneus, and/or temporoparietal cortices) on FDG-PET, and (3) cortical thinning/gray matter loss in a specific anatomic distribution (i.e., lateral and medial parietal, posterior cingulate, and lateral temporal cortices) and/or hippocampal atrophy on volumetric MRI. Other markers include, but are not limited to fMRI measures of default network connectivity. In certain embodiments early synaptic dysfunction, as assessed by functional imaging techniques such as FDG-PET and fMRI, can be detectable before volumetric loss. Without being bound to a particular theory, it is believed that amyloid-positive individuals with evidence of early neurodegeneration may be farther down the trajectory (i.e., in later stages of preclinical (asymptomatic) AD).

In certain embodiments the subjects suitable for the prophylactic methods contemplated herein include, but are not limited to, subjects characterized as amyloid positive with evidence of neurodegeneration and subtle cognitive decline. Without being bound to a particular theory, it is believed that those individuals with biomarker evidence of amyloid accumulation, early neurodegeneration, and evidence of subtle cognitive decline are in the last stage of preclinical (asymptomatic) AD, and are approaching the border zone with clinical criteria for mild cognitive impairment (MCI). These individuals may demonstrate evidence of decline from their own baseline (particularly if proxies of cognitive reserve are taken into consideration), even if they still perform within the "normal" range on standard cognitive measures. Without being bound to a particular theory, it is believed that more sensitive cognitive measures, particularly with challenging episodic memory measures, may detect very subtle cognitive impairment in amyloid-positive individuals. In certain embodiments criteria include, but are not limited to, self-complaint of memory decline or other subtle neurobehavioral changes.

As indicated above, subjects/patients amenable to prophylactic methods described herein include individuals at risk of disease (e.g., a pathology characterized by amyloid plaque formation such as MCI) but not showing symptoms, as well as subjects presently showing certain symptoms or markers. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see Hardy (1997) *Trends. Neurosci.*, 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al. (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., at about 20, about 30, about 40, about 50 years of age). Usually, however, it is not necessary to begin treatment until a patient reaches at least about 40, or at least about 50, or at least about 55, or at least about 60, or at least about 65, or at least about 70 years of age.

In some embodiments, the subject exhibits symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is diagnosed as having MCI. Increased levels of neural thread protein (NTP) in urine and/or increased levels of α2-macroglobulin (α2M) and/or complement factor H (CFH) in plasma are also biomarkers of MCI and/or AD (see, e.g., Anoop et al. (2010) *Int. J. Alzheimer's Dis.* 2010:606802).

In certain embodiments, subjects amenable to treatment may have age-associated memory impairment (AAMI), or mild cognitive impairment (MCI). The methods described herein are particularly well-suited to the prophylaxis and/or treatment of MCI. In such instances, the methods can delay or prevent the onset of MCI, and or reduce one or more symptoms characteristic of MCI and/or delay or prevent the progression from MCI to early-, mid- or late-stage Alzheimer's disease or reduce the ultimate severity of the disease.

Mild Cognitive Impairment (MCI)

Mild cognitive impairment (MCI, also known as incipient dementia, or isolated memory impairment) is a diagnosis given to individuals who have cognitive impairments beyond that expected for their age and education, but that typically do not interfere significantly with their daily activities (see, e.g., Petersen et al. (1999) *Arch. Neurol.* 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al. (2004) *Arch. Neurol.* 61(1): 59-66; and on the interne at en.wikipedia.org/wiki/Mild_cognitive_impairment-cite_note-Grundman-1). When individuals have impairments in domains other than memory it is often classified as non-amnestic single- or multiple-domain MCI and these individuals are believed to be more likely to convert to other dementias (e.g., dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al. (2006) *Arch. Neurol.* 63(5): 665-72).

The diagnosis of MCI typically involves a comprehensive clinical assessment including clinical observation, neuroimaging, blood tests and neuropsychological testing. In certain embodiments diagnostic criteria for MIC include, but are not limited to those described by Albert et al. (2011) *Alzheimer's & Dementia*. 1-10. As described therein, diagnostic criteria include (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings.

In certain embodiments clinical evaluation/diagnosis of MCI involves: (1) Concern reflecting a change in cognition reported by patient or informant or clinician (i.e., historical or observed evidence of decline over time); (2) Objective evidence of Impairment in one or more cognitive domains, typically including memory (i.e., formal or bedside testing to establish level of cognitive function in multiple domains); (3) Preservation of independence in functional abilities; (4) Not demented; and in certain embodiments, (5) An etiology of MCI consistent with AD pathophysiological processes. Typically, vascular, traumatic, and medical causes of cognitive decline, are ruled out where possible. In certain embodiments, when feasible, evidence of longitudinal decline in cognition is identified. Diagnosis is reinforced by a history consistent with AD genetic factors, where relevant.

With respect to impairment in cognitive domain(s), there should be evidence of concern about a change in cognition, in comparison with the person's previous level. There should be evidence of lower performance in one or more cognitive domains that is greater than would be expected for the patient's age and educational background. If repeated assessments are available, then a decline in performance should be evident over time. This change can occur in a variety of cognitive domains, including memory, executive function, attention, language, and visuospatial skills. An impairment in episodic memory (i.e., the ability to learn and retain new information) is seen most commonly in MCI patients who subsequently progress to a diagnosis of AD dementia.

With respect to preservation of independence in functional abilities, it is noted that persons with MCI commonly have mild problems performing complex functional tasks which they used to perform shopping. They may take more time, be less efficient, and make more errors at performing such activities than in the past. Nevertheless, they generally maintain their independence of function in daily life, with minimal aids or assistance.

With respect to dementia, the cognitive changes should be sufficiently mild that there is no evidence of a significant impairment in social or occupational functioning. If an individual has only been evaluated once, change will be inferred from the history and/or evidence that cognitive performance is impaired beyond what would have been expected for that individual.

Cognitive testing is optimal for objectively assessing the degree of cognitive impairment for an individual. Scores on cognitive tests for individuals with MCI are typically 1 to 1.5 standard deviations below the mean for their age and education matched peers on culturally appropriate normative data (i.e., for the impaired domain(s), when available).

Episodic memory (i.e., the ability to learn and retain new information) is most commonly seen in MCI patients who subsequently progress to a diagnosis of AD dementia. There are a variety of episodic memory tests that are useful for identifying those MCI patients who have a high likelihood of progressing to AD dementia within a few years. These tests typically assess both immediate and delayed recall, so that it is possible to determine retention over a delay. Many, although not all, of the tests that have proven useful in this regard are wordlist learning tests with multiple trials. Such tests reveal the rate of learning over time, as well as the maximum amount acquired over the course of the learning trials. They are also useful for demonstrating that the individual is, in fact, paying attention to the task on immediate recall, which then can be used as a baseline to assess the relative amount of material retained on delayed recall. Examples of such tests include (but are not limited to: the Free and Cued Selective Reminding Test, the Rey Auditory Verbal Learning Test, and the California Verbal Learning Test. Other episodic memory measures include, but are not limited to: immediate and delayed recall of a paragraph such as the Logical Memory I and II of the Wechsler Memory Scale Revised (or other versions) and immediate and delayed recall of nonverbal materials, such as the Visual Reproduction subtests of the Wechsler Memory Scale-Revised I and II.

Because other cognitive domains can be impaired among individuals with MCI, it is desirable to examine domains in addition to memory. These include, but are not limited to executive functions (e.g., set-shifting, reasoning, problem-solving, planning), language (e.g., naming, fluency, expressive speech, and comprehension), visuospatial skills, and attentional control (e.g., simple and divided attention). Many clinical neuropsychological measures are available to assess these cognitive domains, including (but not limited to the Trail Making Test (executive function), the Boston Naming Test, letter and category fluency (language), figure copying (spatial skills), and digit span forward (attention).

As indicated above, genetic factors can be incorporated into the diagnosis of MCI. If an autosomal dominant form of AD is known to be present (i.e., mutation in APP, PS1, PS2), then the development of MCI is most likely the precursor to AD dementia. The large majority of these cases develop early onset AD (i.e., onset below 65 years of age).

In addition, there are genetic influences on the development of late onset AD dementia. For example, the presence of one or two ε4 alleles in the apolipoprotein E (APOE) gene is a genetic variant broadly accepted as increasing risk for late-onset AD dementia. Evidence suggests that an individual who meets the clinical, cognitive, and etiologic criteria for MCI, and is also APOE ε4 positive, is more likely to progress to AD dementia within a few years than an individual without this genetic characteristic. It is believed that additional genes play an important, but smaller role than APOE and also confer changes in risk for progression to AD dementia (see, e.g., Bertram et al. (2010) *Neuron*, 21: 270-281).

In certain embodiments subjects suitable for the prophylactic methods described herein include, but need not be limited to, subjects identified having one or more of the core clinical criteria described above and/or subjects identified with one or more "research criteria" for MCI, e.g., as described below.

"Research criteria" for the identification/prognosis of MCI include, but are not limited to biomarkers that increase the likelihood that MCI syndrome is due to the pathophysiological processes of AD. Without being bound to a particular theory, it is believed that the conjoint application of clinical criteria and biomarkers can result in various levels of certainty that the MCI syndrome is due to AD pathophysiological processes. In certain embodiments, two categories of biomarkers have been the most studied and applied to clinical outcomes are contemplated. These include "Aβ" (which includes CSF Aβ$_{42}$ and/or PET amyloid imaging) and "biomarkers of neuronal injury" (which include, but are not limited to CSF tau/p-tau, hippocampal, or medial temporal lobe atrophy on MRI, and temporoparietal/precuneus hypometabolism or hypoperfusion on PET or SPECT).

Without being bound to a particular theory, it is believed that evidence of both AP, and neuronal injury (either an increase in tau/p-tau or imaging biomarkers in a topographical pattern characteristic of AD), together confers the highest probability that the AD pathophysiological process is present. Conversely, if these biomarkers are negative, this may provide information concerning the likelihood of an alternate diagnosis. It is recognized that biomarker findings may be contradictory and accordingly any biomarker combination is indicative (an indicator) used on the context of a differential diagnosis and not itself dispositive. It is recognized that varying severities of an abnormality may confer different likelihoods or prognoses, that are difficult to quantify accurately for broad application.

For those potential MCI subjects whose clinical and cognitive MCI syndrome is consistent with AD as the etiology, the addition of biomarker analysis effects levels of certainty in the diagnosis. In the most typical example in which the clinical and cognitive syndrome of MCI has been established, including evidence of an episodic memory disorder and a presumed degenerative etiology, the most likely cause is the neurodegenerative process of AD. However, the eventual outcome still has variable degrees of certainty. The likelihood of progression to AD dementia will vary with the severity of the cognitive decline and the nature of the evidence suggesting that AD pathophysiology is the underlying cause. Without being bound to a particular theory it is believed that positive biomarkers reflecting neuronal injury increase the likelihood that progression to dementia will occur within a few years and that positive findings reflecting both Aβ accumulation and neuronal injury together confer the highest likelihood that the diagnosis is MCI due to AD.

A positive Aβ biomarker and a positive biomarker of neuronal injury provide an indication that the MCI syndrome is due to AD processes and the subject is well suited for the methods described herein.

A positive Aβ biomarker in a situation in which neuronal injury biomarkers have not been or cannot be tested or a positive biomarker of neuronal injury in a situation in which Aβ biomarkers have not been or cannot be tested indicate an intermediate likelihood that the MCI syndrome is due to AD. Such subjects are believed to be is well suited for the methods described herein Negative biomarkers for both Aβ and neuronal injury suggest that the MCI syndrome is not due to AD. In such instances the subjects may not be well suited for the methods described herein.

There is evidence that magnetic resonance imaging can observe deterioration, including progressive loss of gray matter in the brain, from mild cognitive impairment to full-blown Alzheimer disease (see, e.g., Whitwell et al. (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al. (2008) *Brain* 131(Pt 3): 665-680).

In certain embodiments, MCI is typically diagnosed when there is 1) Evidence of memory impairment; 2) Preservation of general cognitive and functional abilities; and 3) Absence of diagnosed dementia.

In certain embodiments MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The information to make each rating can be obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 2.

TABLE 2

Illustrative clinical dementia rating (CDR) table.

| Impairment: | None | Questionable | Mild | Moderate | Severe |
|---|---|---|---|---|---|
| CDR: | 0 | 0.5 | 1 | 2 | 3 |
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |

TABLE 2-continued

Illustrative clinical dementia rating (CDR) table.

| Impairment:<br>CDR: | None<br>0 | Questionable<br>0.5 | Mild<br>1 | Moderate<br>2 | Severe<br>3 |
|---|---|---|---|---|---|
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home<br>Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild bit definite impairment of function at home; more difficult chores abandoned; more complicated hobbies and interests abandoned | Only simple chores preserved; very restricted interests, poorly maintained | No significant function in home |
| Personal Care | Fully capable of self-care | | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In certain embodiments use of the phototherapy devices and/or systems described herein is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al. (2004) *Arch Neurol* 61: 59-66, report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemorycognitive measures included in the battery. Tests of learning, attention, perceptual speed, category fluency, and executive function may be impaired in patients with MCI, but these are far less prominent than the memory deficit.

Alzheimer's Disease (AD)

In certain embodiments the phototherapy devices and/or systems described herein are contemplated for the treatment of Alzheimer's disease. In such instances the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, it is believed the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's Criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al. (1984) *Neurology* 34(7): 939-44. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al. (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al. (1984) *Am. J. Psychiatr.*, 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al. supra). Any score greater than or equal to 25 points (out of 30) is effectively normal (intact). Below this, scores can indicate severe (≤9 points), moderate (10-20 points) or mild (21-24 points) Alzheimer's disease.

Alzheimer's disease can be broken down into various stages including: 1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 3.

TABLE 3

Illustrative stages of Alzheimer's disease.

Moderate Cognitive Decline (Mild or early stage AD)

At this stage, a careful medical interview detects clear-cut deficiencies in the following areas:
Decreased knowledge of recent events.
Impaired ability to perform challenging mental arithmetic. For example, to count backward from 100 by 7s.
Decreased capacity to perform complex tasks, such as marketing, planning dinner for guests, or paying bills and managing finances.
Reduced memory of personal history.
The affected individual may seem subdued and withdrawn, especially in socially or mentally challenging situations.
Moderately severe cognitive decline (Moderate or mid-stage Alzheimer's disease)

Major gaps in memory and deficits in cognitive function emerge. Some assistance with day-to-day activities becomes essential. At this stage, individuals may:
Be unable during a medical interview to recall such important details as their current address, their telephone number, or the name of the college or high school from which they graduated.
Become confused about where they are or about the date, day of the week or season.
Have trouble with less challenging mental arithmetic; for example, counting backward from 40 by 4s or from 20 by 2s.
Need help choosing proper clothing for the season or the occasion.
Usually retain substantial knowledge about themselves and know their own name and the names of their spouse or children.
Usually require no assistance with eating or using the toilet.
Severe cognitive decline (Moderately severe or mid-stage Alzheimer's disease)

Memory difficulties continue to worsen, significant personality changes may emerge, and affected individuals need extensive help with daily activities. At this stage, individuals may:
Lose most awareness of recent experiences and events as well as of their surroundings.
Recollect their personal history imperfectly, although they generally recall their own name.
Occasionally forget the name of their spouse or primary caregiver but generally can distinguish familiar from unfamiliar faces.
Need help getting dressed properly; without supervision, may make such errors as putting pajamas over daytime clothes or shoes on wrong feet.
Experience disruption of their normal sleep/waking cycle.
Need help with handling details of toileting (flushing toilet, wiping and disposing of tissue properly).

TABLE 3-continued

Illustrative stages of Alzheimer's disease.

Have increasing episodes of urinary or fecal incontinence.
Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding.
Tend to wander and become lost.
Very severe cognitive decline (Severe or late-stage Alzheimer's disease)

This is the final stage of the disease when individuals lose the ability to respond to their environment, the ability to speak, and, ultimately, the ability to control movement.
Frequently individuals lose their capacity for recognizable speech, although words or phrases may occasionally be uttered.
Individuals need help with eating and toileting and there is general incontinence.
Individuals lose the ability to walk without assistance, then the ability to sit without support, the ability to smile, and the ability to hold their head up. Reflexes become abnormal and muscles grow rigid.
Swallowing is impaired.

In various embodiments the use of the phototherapy devices and/or systems described herein is deemed effective when the there is a reduction in the CSF of levels of one or more components selected from the group consisting of Tau, phospho-Tau (pTau), APPneo, soluble Aβ40, soluble Aβ42, and/or and Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments subjects amenable to the present methods generally are free of a neurological disease or disorder other than Alzheimer's disease. For example, in certain embodiments, the subject does not have and is not at risk of developing a neurological disease or disorder such as Parkinson's disease, and/or schizophrenia, and/or psychosis.

The foregoing uses are illustrative and non-limiting. Using the teaching provided herein, numerous other applications of the phototherapy devices and/or systems described herein will be available to one of skill in the art.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device, said device comprising:
a first light source that produces a light that comprises or consists of a blue spectral component and/or green spectral component wherein light comprising said blue and/or green spectral component is a blinking light; and
a second light source comprising a blinking light source that produces a light lacking a blue and/or green spectral component or where the blue and/or green spectral component produced by said second light source is smaller than the blue and/or green spectral component of the light produced by said first light source;
wherein said first light source and said second light source are configured to emit light in substantially the same direction to provide illumination that is the combination of illumination from said first light source and said second light source wherein:
i) the color temperature difference (ΔT) between the first light source and the second light source is about 50K or less;
ii) for each light source the distance to a black-body locus ($D_{uv}$) is less than about 0.01,
iii) the difference in intensity between the first light source and the second light source is less than about 100 lux; and
iv) the difference in illumination angle between the first light source and the second light source is less than about 30 degrees;
so that looking directly into the two lamps with the human eye, the two light sources will appear substantially identical in color and intensity; and
a controller that is configured to control a blink frequency of said first light source and the a blink frequency of said second light source, a phase delay between blinking of said first light source, and a duty cycle of said first light source and said second light source, and wherein:
said controller is configured to provide continuous blinking of said first light source and said second light source when said device is turned on; and
said controller is configured to control the blinking of said first light source and said second light source so that the blinking of said first light source and the blinking of said second light source are 180 degrees out of phase with each other to produce a combined illumination that has a substantially constant illumination intensity and color.

2. The device of claim 1, wherein:
said first light source produces a light that comprises or consists of a blue spectral component; and
said second light source that produces a light lacking a blue spectral component or where the blue spectral component produced by said second light source is smaller than the blue spectral component of the light produced by said first light source.

3. The device of claim 2, wherein a blue light comprising said first light source, or the blue spectral component of said first light source, is in the wavelength range from about 440 nm up to about 495 nm.

4. The device of claim 3, wherein the blue light comprising said first light source, or the blue spectral component of said first light source has a maximum emission at about 460 nm.

5. The device of claim 2, wherein said first light source provides an irradiance that is larger than 5 mW/nm/m² in a wavelength range from 440 nm up to 500 nm.

6. The device of claim 1, wherein:
said first light source blinks at a frequency that ranges from about 20 Hz up to about 50 Hz; and
said second light source blinks at a frequency that ranges from about 20 Hz up to about 50 Hz.

7. The device of claim 6, wherein said first light source blinks at a frequency of about 40 Hz and said second light source blinks at a frequency of about 40 Hz.

8. The device of claim 7, wherein said first light source provides a luminous intensity ranging from 10 lm up to 10,000 lm.

9. The device of claim 6, wherein:
said first light source produces blinks that have a duration that ranges from about 5 ms up to about 20 ms; and
said second light source produces blinks that have a duration that ranges from about 5 ms up to about 20 ms.

10. The device of claim 1, wherein the duty cycle of said first light source and/or said second light source ranges from 5% up to 90%.

11. The device of claim 10, wherein the duty cycle of said first light source and/or said second light source is 50%.

12. The device of claim 1, wherein the ratio of duty cycle of said first light source to said second light source ranges from 1:2 to 2:1.

13. The device of claim 12, wherein the ratio of duty cycle of said first light source to the duty cycle of said second light source is about 1:1.

14. The device of claim 1, wherein:
said first light source has a color temperature that ranges from about 2700K up to about 3500K; and
said second light source has a color temperature that ranges from about 2700K up to about 3500K.

15. The device of claim 14, wherein the difference in color temperature between said first light source and said second light source is less than 30K.

16. The device of claim 14, wherein the difference in color temperature between said first light source and said second light source ranges from 5K up to 10K.

17. The device of claim 16, wherein the difference in color temperature between said first light source and said second light source ranges from 0.5K up to 5K.

18. The device of claim 1, wherein said first light source provides a luminous intensity ranging from 10 lm up to 5,000 lm.

19. The device of claim 1, wherein a distance to the black body locus $D_{UV}$ for said first light source and said second light source is 0.0001 or less.

20. The device of claim 1, wherein the difference in illumination intensity between said first light source and said second light source is less than 100 lux.

21. The device of claim 20, wherein the difference in intensity between said first light source and said second light source is less than 5 lux.

22. The device of claim 21, wherein the difference in intensity between said first light source and said second light source is less than 2 lux.

23. The device of claim 1, wherein said first light source and/or said second light source comprises one or more light emitting diodes (LEDs).

24. The device of claim 23, wherein the first light source and/or the second light source comprises at least one different LED for each spectral component.

25. The device of claim 1, wherein:
said first light source and said second light source are disposed in a diffuser; and/or
said device comprises a luminaire; or
said device comprises a table lamp or an overhead lamp; or
said device is configured for mounting proximate, at, and/or attached to a frame of a window; or
said device comprises a face or eye mask in that directs illumination from both said first light source and said second light source to each eye.

26. A method of treating a subject having a neurodegenerative condition selected from the group consisting of dementia, mild cognitive impairment, and Alzheimer's disease, said method comprising:
using a device of claim 1 to expose said subject to blinking blue light in the wavelength range from 440 nm up to 495 nm at a frequency ranging from 20 Hz up to 60 Hz, at an intensity and duration sufficient to mitigate a symptom, or slow or stop the progression of said neurodegenerative condition; and
where the illumination produced by said second light source supplements the illumination produced by the first light source so that the blinking of said first light source when combined with the light from said second light source is substantially undetectable by said subject.

27. The method of claim 26, wherein the blue light or blue spectral component of a light has a maximum at about 460 nm.

28. The method of claim 26, wherein:
said method comprises ameliorating one or more symptoms of Alzheimer's disease, and/or reversing Alzheimer's disease, and/or reducing the rate of progression of Alzheimer's disease; and/or
said method comprises preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease; and/orsaid method is a method of preventing or delaying the transition from a cognitively asymptomatic pre-Alzheimer's condition to a pre-Alzheimer's cognitive dysfunction; and/or
said method is a method of preventing or delaying the onset of a pre-Alzheimer's cognitive dysfunction, or ameliorating one or more symptoms of a pre-Alzheimer's cognitive dysfunction; and/or
said method comprises preventing or delaying the progression of a pre-Alzheimer's cognitive dysfunction to Alzheimer's disease; and/or
said method produces a reduction in the CSF of levels of one or more components selected from the group consisting of A$\beta$42, sAPP$\beta$, total-Tau (tTau), phospho-Tau (pTau), APPneo, soluble A$\beta$40, pTau/A$\beta$42 ratio and tTau/A$\beta$42 ratio, and/or an increase in the CSF of levels of one or more components selected from the group consisting of A$\beta$42/A$\beta$40 ratio, A$\beta$42/A$\beta$38 ratio, sAPP$\alpha$, sAPP$\alpha$/sAPP$\beta$ ratio, sAPP$\alpha$/A$\beta$40 ratio, and sAPP$\alpha$/A$\beta$42 ratio; and/or
said method produces a reduction of the plaque load in the brain of the subject; and/or
said method produces a reduction in the rate of plaque formation in the brain of the subject; and/or
said method produces an improvement in the cognitive abilities of the subject; and/or
said method produces an improvement in, a stabilization of, or a reduction in the rate of decline of the clinical dementia rating (CDR) of the subject.

29. A method of treating depression, short-term memory loss, of improving memory, of improving cognition, of improving sleep, and/or of improving athletic performance in a subject, and/or synchronizing a circadian rhythm to local time, said method comprising:
using a device of claim 1 to expose said subject to blinking blue light in the wavelength range from about 440 nm up to about 495 nm at a frequency ranging from about 20 Hz up to about 60 Hz, at an intensity and duration sufficient to mitigate a symptom of depression, or to mitigate short-term memory loss, or to improve memory, or to improve cognition, or to improve sleep, and/or to improve athletic performance in said subject; and where the illumination produced by said second light source supplements the illumination produced by the first light source so that the blinking of said first light source when combined with the light from said second light source is substantially undetectable by said subject.

* * * * *